United States Patent [19]
Tomasz et al.

[11] Patent Number: 6,136,587
[45] Date of Patent: *Oct. 24, 2000

[54] AUXILIARY GENES AND PROTEINS OF METHICILLIN RESISTANT BACTERIA AND ANTAGONISTS THEREOF

[75] Inventors: Alexander Tomasz; Herminia De Lencastre, both of New York, N.Y.

[73] Assignee: The Rockefeller University, New York, N.Y.

[*] Notice: This patent issued on a continued prosecution application filed under 37 CFR 1.53(d), and is subject to the twenty year patent term provisions of 35 U.S.C. 154(a)(2).

[21] Appl. No.: 08/678,613

[22] Filed: Jul. 10, 1996

Related U.S. Application Data

[60] Provisional application No. 60/000,984, Jul. 10, 1995.

[51] Int. Cl.[7] .............................. C12N 1/20; C12N 15/00; C07H 21/02; C07H 21/04
[52] U.S. Cl. ..................................... 435/252.3; 435/253.4; 435/320.1; 536/23.1; 536/23.7
[58] Field of Search .............................. 435/253.4, 320.1, 435/252.3; 536/23.1, 23.7

[56] References Cited

U.S. PATENT DOCUMENTS 4,431,739  2/1984  Riggs .

FOREIGN PATENT DOCUMENTS

WO 95/16039  6/1995  WIPO .

OTHER PUBLICATIONS

Wu et al. (1996) Microb. Drug Resist. 2:277–85.
Berger–Bachi (1994) Trends in Microbiol. 2:389–92.
De Lencastre et al. (1994) Antimicrob. Agent. Chemother. 38:2590–8.
De Lencastre et al. (1994) Eur. J. Clin. Microbiol. Infect. Dis. 13:64–73.
De Lencastre et al. (1994) J. Antimicrob. Chemother. 33:7–24.
Ornelas–Soares et al. (1994) J. Biol. Chem. 269:27246–50.
De Jonge et al. (1993) Animicrob. Agents Chemother. 37:342–6.
De Jonge et al. (1993) J. Bacteriol. 1751:2779–82.
Gustafson (1993) Abst. 93rd Gen. Meet. Am. Soc. Microbiol., A–97, p. 18.
Henze et al. (1993) J. Bacteriol. 175:1612–20.
Ornelas–Soares et al. (1993) J. Biol. Chem. 268:26268–72.
Berger–Bachi et al. (1992) Antimicrob. Agents Chemotherapy 36:1367–73.
De Jonge et al. (1992) J. Biol. Chem. 267:11248–54.
De Jonge et al. (1992) J. Biol. Chem. 267:11255–9.
Oshida et al. (1992) J. Bacteriol. 174:4952–9.
Wenzel et al. (1992) Am. J. Med. 91(Supp. 3B):221–7.
Blumberg et al. (1991) J. Inf. Disease 63:1279–85.
De Jonge et al. (1991) J. Bacteriol. 173:1105–10.
De Lencastre et al. (1991) Animicrob. Agents Chemother. 35:632–9.
Maidhof et al. (1991) J. Bacteriol. 173:3507–13.
Tomasz et al. (1991) Antimicrobial Agents and Chemotherapy 35:124–9.
Matthews et al. (1990) Antimicrobial Agents and Chemotherapy 34:1777–9.
Matthews et al. (1990) In: Molecular Biology of the Staphylococci, Novick and Skurray, Eds., VCH Publishers; New York, pp. 69–83.
Tomasz, (1990) In: Molecular Biology of the Staphylococci, Novick and Skurray, Eds., VHC Publishers: New York, pp. 565–583.
Murakami et al. (1989) J. Bacteriol. 171:874–9.
Leclercq et al. (1988) New Eng. J. Med. 319:157–61.
Hartman et al. (1986) Animicrob. Agents Chemother. 30:29:85–92.
Tonin et al. (1986) Animicrob. Agents Chemother. 30:577–83.
Beck et al. (1985) J. Bacteriol. 165:373–8.
Berger–Bachi (1983) J. Bacteriol. 154:479–87.
Basheer et al. (Nucleic Acids Research vol. 19 No. 18 pp. 4921–4924), 1991.
Ornelas–Soares et al. (J. of Biol. Chem. vol. 269 No. 44 pp. 27246–27250), Nov. 4, 1994.
Oshida et al. (J. of Bacteriology vol. 174 No. 15 pp. 4952–4959), Aug. 1992.
Berger–Bachi et al. Antimicrobial Agents & Chemo. vol. 36 No. 7 pp. 1367–1373, Jul. 1992.
Tanaka et al. (Science vol. 242 pp. 1040–1042), Nov. 18, 1988.

*Primary Examiner*—Albert Navarro
*Attorney, Agent, or Firm*—Klauber & Jackson

[57] ABSTRACT

The present invention is directed to the identification of mutant strains of methicillin resistant bacteria, in particular methicillin resistant *Staphylococcus aureus*, to identify the characteristics of such bacteria and develop drugs that can reverse, inhibit, or reduce bacterial resistance to beta lactam antibiotics, e.g., methicillin. The invention particularly relates to identification of a novel mutant strain of methicillin resistant *S. aureus* that manifests a unique phenotype. Accordingly, the invention provides for methods of treatment and corresponding pharmaceutical compositions for treating bacterial, particularly staphylococcal, infections.

7 Claims, 16 Drawing Sheets

FIG. 11A-1

```
            AAGATAAATATTTTAATAAGTAGGAGTGTAATGAAATGAATCTTAATATAGAAACAACC
  1         ------+---------+---------+---------+---------+---------+   60
            ACTCAAGATAAATTTACGAAGTAAAGTCGGTGGAGAATTAGATGTTTATACTGTGCCT
 61         ------+---------+---------+---------+---------+---------+  120
            GAATTAGAAGAGGTTTTAACACCTATGAGACAAGATGGAACTCGTGATATTTATGTTAAT
121         ------+---------+---------+---------+---------+---------+  180
            TTAGCAAATGTGAGTTATATGGATTCGACAGGTTTAGGTTTATTCGTAGGTACATTAAAA
181         ------+---------+---------+---------+---------+---------+  240
            GCATTAAACCAAAATGATAAAGAACTATACATTTTAGGTGTCAGATCGTATCGGTAGA
241         ------+---------+---------+---------+---------+---------+  300
            CTATTTGAAATTACTGGTCTTAAGGATTAATGCATGTTAATGAAGGAACGGAGGTCGAA
301         ------+---------+---------+---------+---------+---------+  360
            TAACATGCAATCTAAAGAAGATTTATCGAAATGCGCGTGCCAGCATCGGCAGAGTATGT
361         ------+---------+---------+---------+---------+---------+  420
            AAGTTTAATTCGTTTAACACTTTCTGGGCGTTTTTTCGAGAGCTGGTGCTACATATGATGA
421         ------+---------+---------+---------+---------+---------+  480
            TATTGAAGATGCCAAGATTGCAGTTAGTGAAGCTGTGACAAATGCAGTTAAACATGCATA
481         ------+---------+---------+---------+---------+---------+  540
            CAAAGAAAATAACAATGTGGGCATTATTAACATATATTTGAAATTTTAGAAGATAAAAT
541         ------+---------+---------+---------+---------+---------+  600
            TAAAATTGTTATTTCTGATAAAGGTGACAGTTTTGATTATGAAACAACTAAATCAAAAAT
601         ------+---------+---------+---------+---------+---------+  660
```

FIG. 11A-2

```
     AGGTCCTTACGATAAAGACGAAAATATAGACTTTTTACGGAAGGTGGCCTAGGTTTATT
661  ------+---------+---------+---------+---------+---------+   720
     TTTAATCGAATCTTTAATGGATGAAGTCACAGTATATAAAGAATCTGGTGTGACAATCAG

TATGACTAAGTATATAAAAAAGAGCAGGTGCGAAATAATGGCGAAAGAGTCGAAATCAG
721  ------+---------+---------+---------+---------+---------+   780
     CTAATGAAATTTCACCTGAGCAAATTAACCAATGGATTAAAGAACACCAAGAAAATAAGA

ATACAGATGCACAGGATAAGTTAGTTAAACATTACCAAAACTAATTGAGTCATTGGCAT
781  ------+---------+---------+---------+---------+---------+   840
     ATAAATATTCTAAAGACAATCACATCACGAAGATTTAGTTCAAGTTGGTATGGTTGGTT

TAATAGGTGCCATAAATAGATTCGATATGTCCTTTGAACGGAAGTTTGAAGCCTTTTTAG
841  ------+---------+---------+---------+---------+---------+   900
     TACCTACTGTAATCGGTGAAATCAAAAAGATATCTACGAGATAAAACTTGGAGTGTACATG

TTCCGAGACGTATTAAAGAATTGGGCCAAGAATCAAAAAAGTGAGCGATGAACTAACCG
901  ------+---------+---------+---------+---------+---------+   960
     CTGAATTAGAGCCGTTCACCTTCTATCAGTGAAATAGCTGATCGATTAGAAGTCTCAGAAG

AAGAAGTGTTAGAAGCAATGGAAATGGGACAAAGTTATAATGCGTTAAGTGTTGATCATT
961  ------+---------+---------+---------+---------+---------+   1020
     CCATTGAAGCTGATAAAGATGGTTCAACTGTTACGCTATTAGATATTATGGGCAACAAG
```

(Positions 1021–1380 continue with similar alignment markers)

FIG. 11B-1

```
      ATGACCATTATGACTTAACTGAAAAACGTATGATTTAGAAAAAATATTACCTATATTAT
1381  ------+---------+---------+---------+---------+---------+  1440
      CTGATCGCGAACGAGAAATCATACAATGTACGTTTATTGAAGGATTGAGTCAAAAGAGA
1441  ------+---------+---------+---------+---------+---------+  1500
      CAGGTGAGCGTATCGGTTAAGTCAAATGCATGTATCACGACTTCAGAGAACGGCAATTA
1501  ------+---------+---------+---------+---------+---------+  1560
      AGAAATTACAAGAAGCAGCACATCAATAGAATTTGTTTATTAATGATACGTTTATAATG
1561  ------+---------+---------+---------+---------+---------+  1620
      AAAAATCCATATAATTATCCCTGATTATTAAATTGAAATCGAGGGGTATTTTAATTTA
1621  ------+---------+---------+---------+---------+---------+  1680
      ATTAAGATTTCGAATAATAATTAAGTGTAGTTTAATGTGTATCCACATAAATGTC
1681  ------+---------+---------+---------+---------+---------+  1740
      GCGATATAGTATTAATAATTAAGTGAAGAAGATATCTAATTGTCGTTTTAAATAGGTGG
1741  ------+---------+---------+---------+---------+---------+  1800
      GTTGCTATTAGAATAAAAAAGTAGTCTTAGATTATGAAATTTAGAAATGATGGTGTGTC
1801  ------+---------+---------+---------+---------+---------+  1860
      ATTTCAATAATCTTAGTGCGTTTAAAATATAGTATGACCTAATCATTCGTTTTAAATG
1861  ------+---------+---------+---------+---------+---------+  1920
      TTTTGGAAGTGAAATTACATTAAGTATCATACCTTAATAGAAGTATTTTAGAATATGTT
1921  ------+---------+---------+---------+---------+---------+  1980
      AAAATAAATGAGTAAATTTAAGAAAAAGTGTGGGTTAAGTAAATGGACAATCAATTGATT
1981  ------+---------+---------+---------+---------+---------+  2040
      AATTCAATCATAGAGAAATATCAATTTAGTAAAAACAAATTGAAGCAGTATTAACACTG
2041  ------+---------+---------+---------+---------+---------+  2100
```

FIG. 11B-2

```
2101 CTAGAAGAAAAAAATACAGTACCATTTATTGCGAGGTATCGAAAAGAGCAAACTGGTGGA 2160
2161 CTAGATGAAGTTCAAATAAAGCAAATTGATGACGAATACCAATATATGGTCAATTTACAA 2220
2221 AAACGTAAAGAAGAAGTTATCAAAATATAGAACAGCAAGGATTACTTACTGAGGAATTA 2280
2281 AAGAAGGATATTTTAAAACAGAATACAAGAACAAATTACAACGTGTTGAAGACCTATATAGGCCTTTT 2340
2341 AAACAAAAGAAAAAGACAAGGGCAACTCGAGGCGAAACGTAAAGGGTTAGAGCCATTAGCG 2400
2401 ATATGGATGAAGGCACGTAAACATGAAGTCTCAATTGAAGAAAAGCACAACAATTTATA 2460
2461 AATGAAGAAGTGCAATCGGTTGAAGATGCTATCAAAGGTGCACAAGATATTATTGCGGAA 2520
2521 CAAATTTCAGATAATCCTAAATATAGAACAAAAATTTAAAAGATATGTATCATCAAGGT 2580
2581 GTGTTAACTACATCTAAAAAAGAAAAATGCTGAAGATGAAAAAGGTATTTTTGAAATGTAC 2640
2641 TATGCATATAGTGAGCCAATTAAACGCATTGCTAATCATAGAGTTTTAGCTGTTAATCGT 2700
2701 GGTGAAAAGAGAGAAAGTTATCTCGCAAGTTTGAATTC 2739
```

AUXILIARY GENES AND PROTEINS OF METHICILLIN RESISTANT BACTERIA AND ANTAGONISTS THEREOF

This application claims priority to provisional application 60/000,984 filed Jul. 10, 1995.

The research leading to the instant Application was supported by National Institutes of Health Grant No. RO1 AI16794. The Government may have certain rights in the invention.

FIELD OF THE INVENTION

The present invention relates to the identification of auxiliary genes that encode proteins involved in antibiotic resistance in bacteria, and to compounds that can antagonize the activity of such proteins, thereby resensitizing resistant bacteria to antibiotics.

BACKGROUND OF THE INVENTION

Clinical-Epidemiological Background

Methicillin resistant strains of *Staphylococcus aureus* (MRSA) have become first ranking nosocomial pathogens worldwide. These bacteria are responsible for over 40% of all hospital-born staphylococcal infections in large teaching hospitals in the US. Most recently they have become prevalent in smaller hospitals (20% incidence in hospitals with 200 to 500 beds), as well as in nursing homes (Wenzel et al., 1992, Am. J. Med. 91(Supp 3B):221–7). An unusual and most unfortunate property of MRSA strains is their ability to pick up additional resistance factors which suppress the susceptibility of these strains to other, chemotherapeutically useful antibiotics. Such multiresistant strains of bacteria are now prevalent all over the world and the most "advanced" forms of these pathogens carry resistance mechanisms to all but one (vancomycin) of the usable antibacterial agents (Blumberg et al., 1991, J. Inf. Disease (63:1279–85).

A most ominous and recent development is the appearance of a vancomycin resistance mechanism in another nosocomial pathogen—*Enterococcus faecium*—which is known for its ability to transfer from one cell to another plasmid-born resistance factors, such as vancomycin resistance. The arrival of vancomycin resistance to MRSA is only a matter of time. Once this happens, an invasive bacterial pathogen without any antibacterial agent to control it will result. This event would constitute nothing short of a potential public health disaster of immense proportion (Leclercg et al., 1988, New Eng. J. Med. 319:157–61).

The preceding explains the intense interest in the public health and pharmacological community in any new method that promises a usable intervention against MRSA. A more complete explanation of the basis for antibiotic resistance follows.

Molecular Basis of Antibiotic Resistance

The central genetic element of methicillin resistance is the so called mecA gene. This gene is found on a piece of DNA of unknown, non-staphylococcal origin that the ancestral MRSA cell(s) must have acquired from a foreign source. The mecA gene encodes for a penicillin binding protein (PBP) called PBP2A (Murakami and Tomasz, 1989, J. Bacteriol. 171:874–79), which has very low affinity for the entire family of beta lactam antibiotics. In the current view, PBP2A is a kind of "surrogate" cell wall synthesizing enzyme that can take over the vital task of cell wall synthesis in staphylococci when the normal complement of PBPs (the normal catalysts of wall synthesis) can no longer function because thy have become fully inactivated by beta lactam antibiotic in the environment. The critical nature of the mecA gene and its gene product PBP2A for the antibiotic resistant phenotype was best demonstrated by transposon inactivation experiments in which the transposon Tn551 was maneuvered into the mecA gene. The result was a dramatic drop in resistance level from the minimum inhibitory concentration (MIC) value of 1600 $\mu$g/ml in the parental bacterium to the low value of about 4 $\mu$g/ml in the transposon mutant (Matthews and Tomasz, 1990, Antimicrobial Agents and Chemotherapy 34:1777–9).

This observation is consistent with the foregoing theory. The mutant bacteria with their interrupted mecA gene could no longer synthesize PBP2A; thus the surrogate enzyme needed for the survival in the antibiotic-rich environment was no longer available to catalyze wall synthesis. Consequently, the methicillin susceptibility of the Tn551 mutant dropped to a level approaching the susceptibility of staphylococci without the mecA gene. Methicillin MIC for such bacteria is usually in the vicinity of 1–2 $\mu$/ml.

Auxiliary genes

Additional genetic work resulted in several surprising observations. First it was found that the level of antibiotic resistance could also be dramatically lowered in transposon mutants in which the Tn551 did not interrupt the mecA gene or interfere with the expression of this gene (i.e. the production of PBP2A). Clearly, these mutants were low in resistance for some reason other than an interruption of the functioning of the mecA gene. In fact, it turned out that the great majority of Tn551 insertional mutants with reduced methicillin resistance all continued to produce normal amounts of PBP2A in spite of the fact that their resistance level could be reduced by very large factors, such as dropping from the methicillin MIC of 1600 $\mu$g/ml to a low of 3 $\mu$g/ml.

The first such mutant was isolated in 1983 by Swiss scientists at a time when the nature of methicillin resistance was hardly understood at all (Berger-Bächi, 1983, J. Bacteriol. 154:479–87). Subsequent work in several laboratories have increased the number of these genetic determinants, the common feature of which was that they had an intact mecA gene and yet they had reduced resistance levels to the beta lactam family of antibiotics. The provisional name "auxiliary genes" was proposed for this class of unusual genetic elements to imply that they appeared to perform some essential "helper" function(s) in the expression of high level beta lactam resistance (Tomasz, 1990, *In Molecular Biology of the Staphylococci*, Novick and Skurray, Eds., VHC Publishers: New York, pp. 565–583).

A second surprising observation concerned the number of auxiliary genes that have been identified. By 1993, the number of genetically distinct auxiliary mutants described in the literature had risen to four.

A third set of observations provided clues as to the biochemical nature of auxiliary functions. It was shown by a newly developed high resolution chromatography technique that many of the auxiliary mutants produced abnormal peptidoglycan in their cell walls. Studies combining High Performance Liquid Chromatography (HPLC) and mass spectrometry allowed the identification of the chemical changes that occurred in the mutants (De Jonge et al., 1991, J. Bacteriol. 173:1105–10; De Jonge et al., 1992, J. Biol. Chem. 267:11248–54; De Jonge et al., 1992, J. Biol. Chem 267:11255–9; and De Jonge et al., 1993, J. Bacteriol. 175:2779–82). The cell wall peptidoglycan of auxiliary mutants was composed of muropeptides (cell wall building blocks) either with incomplete cross-linking peptides or containing a free glutamic acid residue instead of the usual isoglutamine. Still other mutants showed different cell wall muropeptide fingerprints in which the exact nature of changes remains to be elucidated. These findings suggest that the auxiliary genes are genes involved with the biosynthesis of cell wall precursor muropeptides.

While all the numerous auxiliary mutants share the common feature of carrying an intact mecA, each one of the auxiliary genes are unique by the criteria of (i) physical location on the chromosome as determined by restriction mapping; (ii) in the several cases in which DNA sequences of the genes were determined (as in the cases of the auxiliary genes known as femA, femB and femC) (Berger-Bächi et al., 1992, Antimicrobial Agents and Chemotherapy 36:1367–73; Gustafson et al., 1993, In *Abstracts of the 93rd General Meeting of the American Society for Microbiology*, Abstract A-97, p. 18; and De Lencastre et al., 1993, "Molecular Aspects of Methicillin resistance in *Staphylococcus aureus*", J. Antimicrob. Chemother. 33:), the genes were shown to have unique DNA sequences; and (iii) in the cases in which the mutants had altered cell wall composition, the HPLC patterns provided additional gene-specific fingerprints characteristic of the particular mutant.

Various references are cited in the Description of the Drawings and the Examples by number. A complete citation for each of such references is found at the end of the specification, after the Examples, and before the claims.

The citation of any reference herein is not an admission that such reference is available as prior art to the instant invention.

SUMMARY OF THE INVENTION

The present invention is broadly directed to the identification of auxiliary genes encoding proteins associated with antibiotic resistance in bacteria, in particular Gram positive bacteria, to characterizing the phenotype of bacteria having mutated auxiliary genes, and to identifying compounds that can mimic the phenotype of bacteria in which the activity of the auxiliary gene is disrupted.

In a preferred aspect, the invention is directed to a mutant antibiotic-resistant *Staphylococcus aureus* strain characterized by increased sensitivity to an antibiotic to which a parent of the mutant strain is resistant, and location of the mutation in a SmaI-C, D, E, F or I fragment of the chromosome of *S. aureus*. Generally, the antibiotic is a beta lactam antibiotic, in particular, methicillin. In a preferred aspect, the mutation is caused by insertion of transposon Tn551.

The present invention particularly relates to mutations in a SmaI-I fragment of the *S. aureus* chromosome.

In a preferred aspect, the mutation occurs in an auxiliary gene and yields a bacterial phenotype with greatly increased sensitivity to methicillin, e.g., a reduction of from 1600 to 12 μg/ml sensitivity. In a specific embodiment, the mutation is to a gene having a high degree of similarity to a σ-factor, such as *Bacillus subtilis* σ-factor.

In a specific embodiment, the mutant antibiotic-resistant *S. aureus* is strain RUSA168.

The invention is further directed to a DNA molecule comprising a nucleic acid sequence which encodes a protein associated with antibiotic resistance in a *S. aureus* bacterium, which nucleic acid sequence is preferably located in the SmaI-I fragment of the chromosome of the *S. aureus* bacterium. In preferred embodiments of the invention, the gene is mutated in mutant strain RUSA168. In a specific embodiment, the gene has a sequence as depicted in FIG. 11.

The invention is also directed to a recombinant vector comprising the DNA molecule described above, operatively associated with an expression control sequence, and to a bacterial cell comprising the recombinant vector.

In another aspect, the invention is directed to a method for identifying a compound useful for sensitizing bacteria to an antibiotic to which the bacterium is resistant, comprising identifying a compound that antagonizes the activity of a protein associated with antibiotic resistance in a *S. aureus* bacterium, which protein is preferably encoded by a nucleic acid sequence located in the SmaI-I fragment of the chromosome of the *S. aureus* bacterium. Preferably, the protein is highly similar to a bacterial σ-factor. Such a σ-factor may, for example, promote transcription of genes encoding proteins involved in synthesis of cell wall compounds. This factor may also be a general stress response protein of staphylococcus that is expressed in response to stimuli such as addition of antibotics.

In one aspect of the invention, the composition and structure of the bacterial cell wall can be analyzed by high performance liquid chromatography and mass spectrometry to determine the association of the protein with muropeptide precursor synthesis. In a specific embodiment, the invention relates to identification of a compound the administration of which results in lack of unsubstituted pentapeptide in the bacterial cell wall, incorporation of alanylglutamate- and alanylisoglutamine-containing muropeptides, and accumulation of large amounts of the UDP-linked muramyul dipeptide in the cytoplasmic wall precursor pool of the mutant bacteria.

In a specific embodiment, the invention contemplates reducing beta lactam antibiotic resistance in bacteria by administration of a competitive inhibitor antagonist of an enzyme or enzymes involved with addition of lysine to the dipeptide alanylisoglutamine and alanylglutamate, such as analogs of isoglutamine, analogs of glutamic acid, analogs of UDP-N-acetylmuramylalanylglutamate, and analogs of lysine.

In yet another aspect, the invention relates to a method for treating a subject suspected of having a bacterial infection comprising administering to the subject an amount of a compound useful for sensitizing the bacteria to an antibiotic to which the bacterium is resistant in conjunction with an amount of the antibiotic sufficient to neutralize the bacteria. In one embodiment, the compound inhibits or antagonizes the activity of a protein associated with muropeptide precursor synthesis, in particular the addition of the third residue in the synthesis of the muropeptide precursor. In another embodiment, the compound inhibits a σ-factor or σ-factor-like protein which is involved in promoting the expression of proteins and which is involved in cellular response to stress.

Although not intending to bound by any particular mechanistic theory or hypothesis, the inventors believe that in the presence of a beta lactam antibiotic the drug molecules and molecules of the cell wall building blocks (muropeptides) compete for the active site of PBP2A, i.e., the surrogate enzyme that, under these conditions, is solely responsible for cell wall biosynthesis. Intact, functioning auxiliary genes allow the production of all the normal cell wall precursor muropeptides, which are highly effective in the competition for the enzyme active site. Thus, in such a staphylococcal cell, relatively higher concentration of the antibiotic is needed for the inactivation of PBP2A, driving the antibiotic MIC value up.

In contrast, inactivated auxiliary genes may prevent the formation of structurally normal cell wall precursors in appropriate intracellular concentrations. Such structurally abnormal—or concentration-wise inadequate—cell wall precursors do not have high enough affinity for the active site of PBP2A. Thus, the relative effectiveness of the drug molecules increases, driving the MIC value down. However, the identification of strains mutated in auxiliary genes which do not appear to be directly associated with muropeptides precursor synthesis suggests that there are interacting cellular pathways involved in antibiotic resistance.

It is a particular advantage of the invention that the compounds of the invention make possible the use of the known battery of antibiotics, rather than requiring development of new antibiotics, for the treatment of bacterial infections.

The primary object of the invention is to identify compounds that reverse antibiotic resistance in bacteria. These compounds can be used in conjunction with the antibiotics to treat bacterial infections not otherwise amenable to chemotherapy.

Thus, it is an object of the present invention to identify auxiliary genes encoding proteins directly or indirectly associated with antibiotic resistance in bacteria.

It is also an object of the invention to identify such auxiliary genes that encode proteins involved with cell wall precursor synthesis.

Yet another object of the invention is to isolate, sequence and characterize such genes, in order to evaluate the functional activity of the protein encoded by the gene.

It is yet a further object to prepare such proteins in purified form for structural and functional analysis.

Most importantly, it is an object of the invention to screen for and select compounds that reverse antibiotic resistance of bacteria.

These and further objects of the invention will become more clear after consideration of the following FIGURES and DETAILED DESCRIPTION.

BRIEF DESCRIPTION OF THE DRAWINGS

(FIG. 1A) Structurally normal precursors are effective competitors driving the methicillin MIC value up. (FIG. 1B) Precursors with abnormal chemical structure, produced in auxiliary mutants, are ineffective competitors with methicillin, resulting in reduced MIC value (and abnormal cell wall composition). The invention is not intended to be limited by this model, which is offered by way of explanation and not limitation.

FIGS. 11A and 11B. Nucleotide sequence which encodes a protein associated with antibiotic resistance in S. aureus strain RUSA168. (SEQ. ID NO:1).

DETAILED DESCRIPTION OF THE INVENTION

Figure 1A:
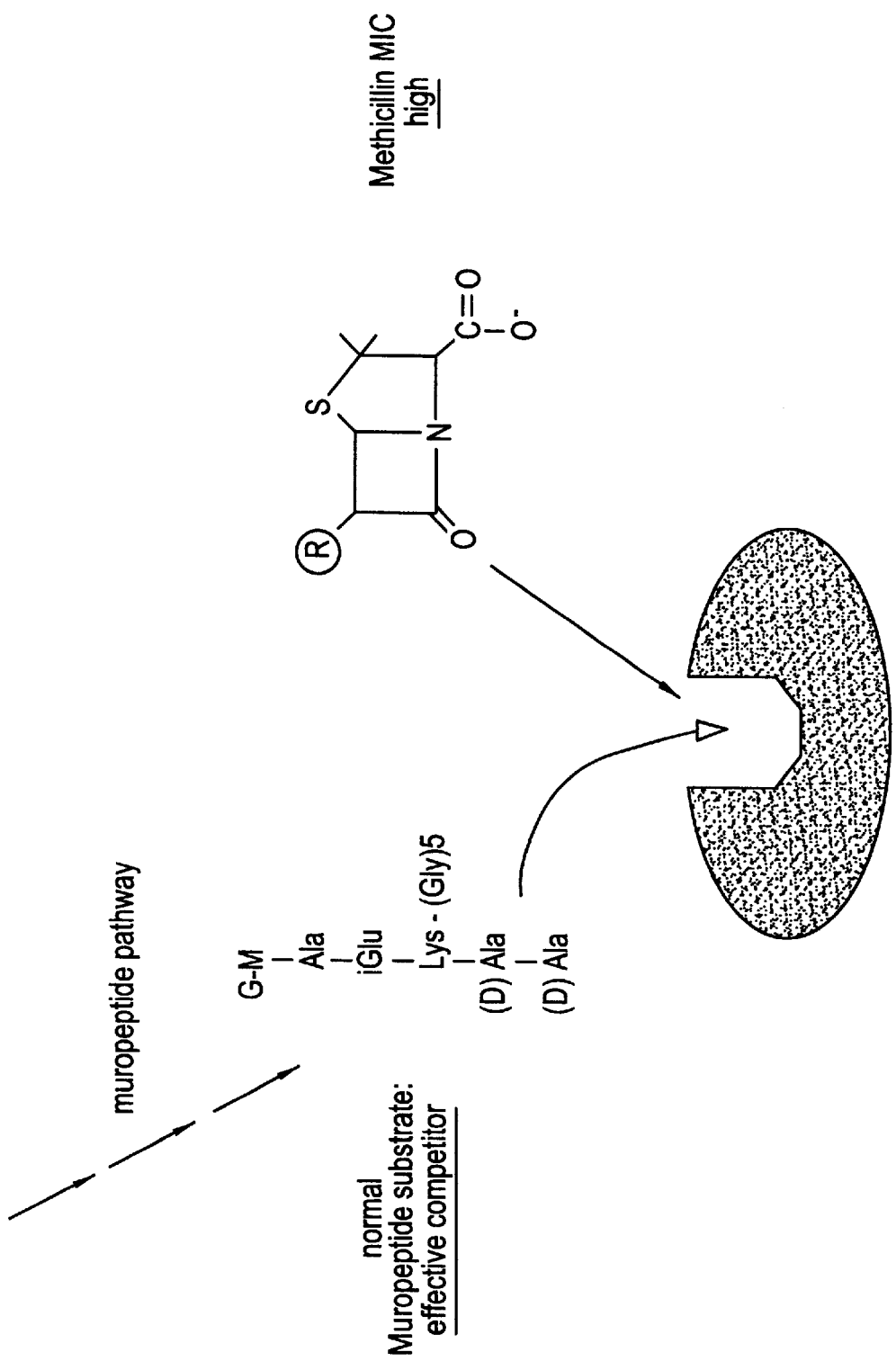
FIGS. 1A and 1B. Proposed model for competition for the active site of penicillin binding protein (PBP) 2A by cell wall precursor muropeptides and antibiotic.
Figure 1B:
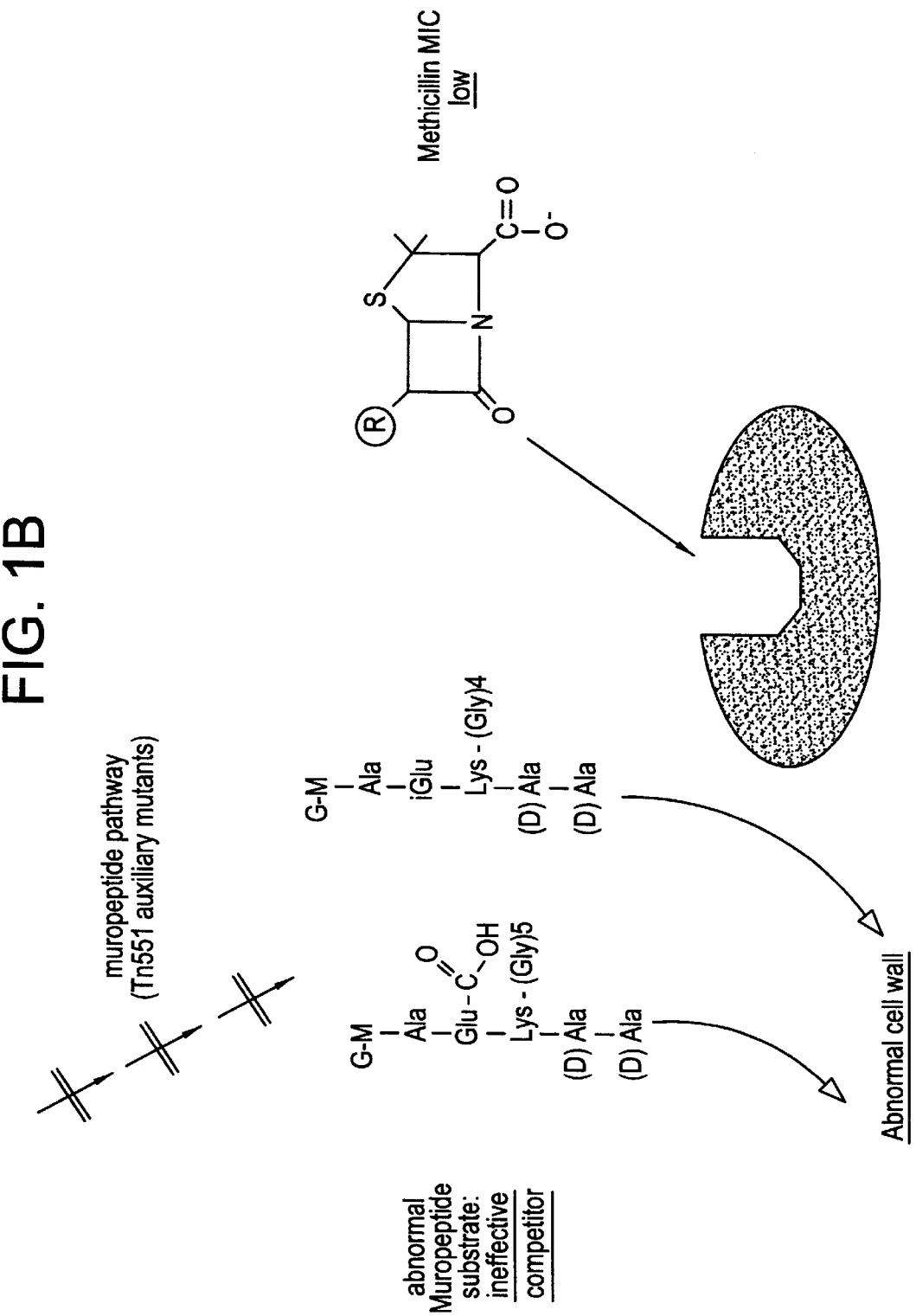

In accordance with the present invention there may be employed conventional molecular biology, microbiology, and recombinant DNA techniques within the skill of the art. Such techniques are explained fully in the literature. See, e.g., Sambrook, Fritsch and Maniatis, "Molecular Cloning: A Laboratory Manual," Second Edition (1989) Cold Spring Harbor Laboratory Press, Cold Spring Harbor, N.Y. (herein "Sambrook et al., 1989"); "DNA Cloning: A Practical Approach," Volumes I and II (D. N. Glover ed. 1985); "Oligonucleotide Synthesis" (M. J. Gait ed. 1984); "Nucleic Acid Hybridization" [B. D. Hames & S. J. Higgins eds. (1985)]; "Transcription And Translation" [B. D. Hames & S. J. Higgins, eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984). Each of these references is specifically incorporated herein by reference.

Therefore, if appearing herein, the following terms shall have the definitions set out below.

A "replicon" is any genetic element (e.g., plasmid, chromosome, virus) that functions as an autonomous unit of DNA replication in vivo, i.e., capable of replication under its own control.

A "vector" is a replicon, such as plasmid, phage or cosmid, to which another DNA segment may be attached so as to bring about the replication of the attached segment.

A cell has been "transformed" by exogenous or heterologous DNA when such DNA has been introduced inside the cell. The transforming DNA may or may not be integrated (covalently linked) into chromosomal DNA making up the genome of the cell. In prokaryotes, yeast, and mammalian cells for example, the transforming DNA may be maintained on an episomal element such as a plasmid.

A "clone" is a population of cells derived from a single cell.

A "nucleic acid molecule" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules") in either single stranded form, or a double-stranded helix. Double stranded DNA—DNA, DNA-RNA and RNA—RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear or circular DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA). A "recombinant DNA molecule" is a DNA molecule that has undergone a molecular biological manipulation.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al., 1989, supra). The conditions of temperature and ionic strength determine the "stringency" of the hybridization. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementarity, variables well known in the art.

A DNA "coding sequence" is a double-stranded DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. If the coding sequence is intended for expression in a eukaryotic cell, a polyadenylation signal and transcription termination sequence will usually be located 3' to the coding sequence.

Transcriptional and translational control sequences are DNA regulatory sequences, such as promoters, enhancers, terminators, and the like, that provide for the expression of a coding sequence in a host cell. In eukaryotic cells, polyadenylation signals are control sequences.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase.

A coding sequence is "under the control" of transcriptional and translational control sequences in a cell when RNA polymerase transcribes the coding sequence into mRNA, which is then translated into the protein encoded by the coding sequence.

An "antisense nucleic acid" is a single stranded nucleic acid molecule which, on hybridizing with complementary bases in an RNA or DNA molecule, inhibits the latter's role. If the RNA is a messenger RNA transcript, the antisense nucleic acid is a countertranscript or mRNA-interfering complementary nucleic acid. As presently used, "antisense" broadly includes RNA—RNA interactions, RNA-DNA interactions, ribozymes and RNase-H mediated arrest. Antisense nucleic acid molecules can be encoded by a recombinant gene for expression in a microorganism, or alternatively they can be prepared synthetically.

A composition comprising "A" (where "A" is a single protein, DNA molecule, vector, etc.) is substantially free of "B" (where "B" comprises one or more contaminating proteins, DNA molecules, vectors, etc.) when at least about 75% by weight of the proteins, DNA, vectors (depending on the category of species to which A and B belong) in the composition is "A". Preferably, "A" comprises at least 90% by weight of the A+B species in the composition, most preferably at least 99% by weight. It is also preferred that a composition, which is substantially free of contamination, contains only a single molecular weight species having the activity or characteristic of the species of interest.

The phrase "pharmaceutically acceptable" refers to molecular entities and compositions that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions.

In its primary specific aspect, the present invention relates to two new *S. aureus* mutants, in which the methicillin MIC value of the paternal MRSA strain COL (MIC 1600 µg/ml) is reduced to between 200 µg/ml and 1.5 µg/ml. Surprisingly, some of these mutations are located on the chromosomal fragments SmaI-B generated by the restriction nuclease SmaI. Other mutations have been found on SmaI-C, D, E, and F, and novel mutations on SmaI-A and I. No auxiliary genes have ever been located to SmaI-B, C, D, E, and F fragments. The mutants are distinct by physical mapping using restriction endonucleases, such as but not limited to PstI, EcoRI, EcoRV, and HindIII. The mutants are valuable; for example, one (RUSA235) causes abnormal cell wall composition.

The invention more generally relates to mutants with mutations to auxiliary genes found in loci in addition to the SmaI-B fragment locus, such as on SmaI-C, D, E, F, and I chromosomal fragments.

The invention relates generally to auxiliary genes and proteins found in loci in addition to the *S. aureus* Sma-B locus. For example, a number of distinct genetic loci involved with the optimal expression of methicillin resistance, including at least fifty-eight distinct loci, found on chromosomal fragments, such as SmaI-B, C, D, E, F and I fragments.

In particular, the invention relates to identification of a gene with a high degree of sequence similarity to a σ-factor, e.g., *B. subtilis* σ-factor. σ-factors function as transcription initiators by binding to promoters. The σ-factor of the invention may be specific for a sub-group of promoters, or may act on a large number of bacterial promoters. The σ-factor may be involved in promoting transcription of proteins involved in the synthesis of bacterial cell components. The σ-factor or σ-factor-like protein may be involved in cellular response to stress, such as the addition of antibiotics.

Identification of Genetic Determinants of Methicillin Resistance

In order to identify the genetic determinants that contribute to the antibiotic, e.g., methicillin, resistance phenotype, mutations can be generated in the isogeneic background of a highly resistant strain. For example, staphylococcal strain COL, a homogeneously and highly methicillin resistant clinical isolated (MIC for methicillin: 1600 mg/L), which is susceptible to erythromycin, can be used as the common parent for all the mutants. In a preferred aspect of the invention, transposon mutagenesis can be used to generate mutants. Alternatively, any random mutagenesis technique known in the art, such as but not limited to chemical mutagenesis, e.g., treatment with alkylating agents, base analogs bisulfate, hydroxylamine, intercalating agents, and the like; radiation; hyperthermia; etc., can be used to develop mutants to identify such genetic determinants.

In a specific preferred embodiment, which is the best mode contemplated by the inventors for identifying auxiliary genes in MRSA, a plasmid carrying transposon Tn551 and a thermosensitive replicator (pRN3208) (Novick, 1974, Mol. Gen. Genetics 135:131–47) can be introduced into COL (Kornblum et al., 1986, Eur. J. Clin. Microbiol. 5:714–8). The plasmid has several heavy metal resistance genes (Cd; Hg; As), the β-lactamase gene and the genetic determinant of erythromycin resistance, the latter being part of the Tn551 transposon. Upon shifting the temperature of the growth medium from 30° C. to 43° C., replication of the plasmid ceases (because of the thermosensitivity of plasmid replication); β-lactamase production and resistance of bacteria to heavy metals is lost along with the plasmid, but a small fraction of the population ($10^{-5}$) retains resistance to erythromycin. This erythromycin resistant group represents Tn551 insertional mutants, i.e., cells in which the Tn551 transposon is rescued by "hopping" from the plasmid into a variety of sites on the staphylococcal chromosome. Insertion of Tn551 is expected to occur more or less randomly, resulting in the inactivation of chromosomal function(s) at the insertion sites, and these inactivated functions may then be identified by appropriate secondary screens (Pattee, 1981, J. Bacteriol., 145:479–88).

In particular, Tn551 mutants of strain COL can be tested for colonies with decreased methicillin resistance. Independent mutant isolates are examined for their methicillin resistance phenotypes. Liquid cultures of the mutants are plated at various cell concentrations on agar plates containing serial dilutions of methicillin. This method, known as population analysis, allows a quantitative description of the antibiotic resistance phenotypes of bacterial cultures in terms of population analysis profiles (PAPs) (de Lencastre et al., 1991, Antimicrobial Agents and Chemotherapy, 35:632–9).

Tn551 insertions can produce profound and unique effects in the expression of methicillin resistance. For example, when the Tn551 is within the mecA gene, the MIC drops from 1600 to 3 mg/L. Cultures of the mutants may demonstrate reduced levels of resistance in the majority of the cells, but the cultures also can become heterogeneous; they may contain subpopulations of cells with dramatically higher resistance levels and with frequencies characteristic of the particular mutant. Conversion of the homogeneous resistance of the parental strain COL to a variety of heterogeneous phenotypes is striking since most clinical isolates are known to have similar heterogeneous PAPs (Tomasz et al., Antimicrobial. Agents and Chemotherapy, 35:124–9).

Transposon mutagenesis can cause chromosomal rearrangements, which may make the interpretation of the Tn551 induced phenotypes difficult. In order to exclude the possibility that a chromosomal rearrangement, and not insertion of Tn551 into a gene, is responsible for observed PAP changes, the mutants can be back-crossed into the original parent strain COL, either by genetic transformation (using DNA prepared from the resistant mutants) or by transduction with phage 80α. After selection for erythromycin resistance (10 mg/L), the transformants can be analyzed for their methicillin resistance. In these crosses the Tn551 inactivated (nonfunctional) gene is expected to replace, by homologous recombination, the corresponding functional gene(s) of COL, recreating the phenotypes of the DNA donor mutant bacteria. Transformants/transductants that have co-transferred with the Tn551 marker the reduced methicillin resistance represent mutants rather than Tn551-induced chromosomal rearrangements.

This technique can yield mutant phenotypes that represent inactivation of a set distinct genetic elements essential for the expression of high level, homogeneous resistance to methicillin.

Chromosomal Location Of Methicillin Resistance Auxiliary Genes

The staphylococcal chromosome can be cut into approximately 16 fragments by using the infrequently cutting restriction endonuclease SmaI, and the physical arrangement of these DNA fragments along a circular structure has been established (Pattee et al., In Molecular Biology of the Staphylococci, 1990, Novick and Skurray, Eds., VCH Publishers; New York, pp. 41–58). Chromosomal DNA from independent Tn551 mutants and from the parent strain COL can be treated with SmaI, and the fragments separated by pulsed field gel electrophoresis. After visualization of the fragment pattern, the DNA fragments can be transferred to nitrocellulose membranes and hybridized with a radiolabeled probe of Tn551. DNA fragments containing the Tn551 light up in the autoradiogram and reveal the location of genetic determinants that are needed for the optimal expression of methicillin resistance.

In a specific embodiment, the auxiliary gene of interest is located in fragment B. No auxiliary gene has previously been identified in fragment B. In a more specific embodiment, the auxiliary gene of interest is the gene mutated in mutant strain RUSA235 or RUSA168.

Chromosomal location can be further resolved after digestion with other restriction enzymes, such as EcoRI, PstI, EcoRV, and HindIII followed by probing with Tn551. For example, the restriction nuclease HindIII cuts the Tn551 transposon at two asymmetrical sites and thereby generates three bands on hybridization.

Mutations to auxiliary genes can be distinguished from mutations to the mecA gene itself. For example, the SmaI fragments and subfragments can be probed to determined if mutation, in particular, Tn551 insertion, has occurred within mecA, as previously characterized (Murakami and Tomasz, 1989, J. Bacteriol., 171:874–79; Matthews and Tomasz, 1990, Antimicrobial Agents and Chemotherapy, 34:1777–9).

Thus, according to the present invention, mutants can be identified for which the reduction of resistance level is due to the inactivation of "auxiliary genes" (Tomasz, 1990, In Molecular Biology of Staphylococci, Novick and Skurray, Eds., VCH Publishes; New York, pp. 565–83), genes that "help" to optimize the resistance phenotype for the bacteria.

The auxiliary genes may be present on the normal bacterial, e.g., staphylococcal, chromosome. Alternatively, auxiliary genes may belong to the package of foreign DNA. In staphylococci, non-staphylococcal DNA may comprise up to 60 kB (Stewart and Rosenblum, 1981, Current Microbiol. 5:227–30; Beck et al., 1985, J. Bacteriol. 165:373–78; Matthews et al., 1990, In Molecular Biology of the Staphylococci, Novick and Skurray, Eds., VCH Publishers; New York, pp. 69–83).

Consistency of phenotypes and the stability of insertion sites in genetic crosses can demonstrate conclusively that the reduction of methicillin resistance levels and the distortion of the mode of expression of resistance in the auxiliary mutants is due to single Tn551 insertions at unique chromosomal sites within genes that are present on the normal staphylococcal chromosome.

Isolation, Cloning, Expression and Characterization of Auxiliary Genes

Any Gram positive bacterial cell potentially can serve as the nucleic acid source for the molecular cloning of an auxiliary gene. The nucleic acid sequences can be isolated from Streptococcus, Bacillus, Mycobacterium, Staphylococcus, Enterococcus, and other Gram positive bacterial sources, etc. In a specific embodiment, the auxiliary gene is found in staphylococci. The DNA may be obtained by standard procedures known in the art from cloned DNA (e.g., a DNA "library"), by chemical synthesis, by cDNA cloning, or by the cloning of genomic DNA, or fragments thereof, purified from the desired cell (See, for example, Sambrook et al., 1989, supra; Glover, D. M. (ed.), 1985, DNA Cloning: A Practical Approach, MRL Press, Ltd., Oxford, U.K. Vol. I, II). Whatever the source, the gene should be molecularly cloned into a suitable vector for propagation of the gene.

In the molecular cloning of the gene from genomic DNA, DNA fragments are generated, some of which will encode the desired gene. The DNA may be cleaved at specific sites using various restriction enzymes. Alternatively, one may use DNAse in the presence of manganese to fragment the DNA, or the DNA can be physically sheared, as for example, by sonication. The linear DNA fragments can then be separated according to size by standard techniques, including but not limited to, agarose and polyacrylamide gel electrophoresis and column chromatography.

Various strategies known in the art can be employed for cloning auxiliary genes identified according to the invention, and the invention is not limited to any particular cloning strategy. In a preferred embodiment, the following basic strategy may be employed: (A) The Tn551 inactivated genes can be cloned in E. coli; (B) the cloned Tn551-carrying pieces of the chromosome can be used to find the active alleles in the parent bacterium, e.g., COL, chromosome; (C) the active alleles can be cloned into a shuttle-vector and assayed for the ability to complement, i.e., correct, the phenotype of the appropriate transposon mutant; and (D) the cloned gene or genes can be sequenced. In a further aspect of the invention, this strategy can be implemented as follows:

(A) Cloning the insertionally inactivated (Tn551) form of auxiliary genes. 1. Digest the chromosomal DNA with different restriction enzymes, preferably selecting enzymes that cut once (or twice) inside Tn551, but that can be used for cloning in the plasmid to be used in the cloning, e.g., the pUC19 plasmid, or BLUESCRIPT. For example, the restriction endonuclease KpnI cuts Tn551 once and can be used with both vectors. The fragments are preferably separated by running in conventional electrophoresis. 2. Probe the fragments with the internal XbaI-HpaI fragment from Tn551 cloned into the plasmid pGEM-1 (plasmid pRT1, see Matthews and Tomasz, 1990, Antimicrob. Agents Chemother. 34:1777–79) to find positive fragments—there will be two if an enzyme that cuts Tn551 once is used. 3. Elute the appropriate fragment or fragments identified with the probe from the gel. 4. Ligate the fragment into an E. coli vector (e.g., pUC19) and transform using an appropriate strain of E. coli as the recipient. 5. Select transformed bacteria in plates containing X-gal and IPTG; colonies containing recombinant plasmids will be white under these conditions. 6. Select the white colonies containing the required chromosomal fragment by colony hybridization using a Tn551 probe, such as the XbaI-HpaI fragment. 7. Identify positive clones identified by probe hybridization and prepare plasmid DNA. 8. Check for the proper size insert in the plasmids. 9. Construct a physical map of the plasmid.

(B) Cloning of the active allele. 1. Prepare a probe from the plasmid carrying part of the Tn551 inactivated gene, i.e., vector+staphylococcus DNA insert+one end of Tn551. 2. Cut the chromosome of the parent strain, e.g., COL, with one of the enzymes used in cloning the fragment, which originates a Tn551-hybridizing fragment of approximately 10 kb. Probe with the plasmid fragment probe and find the positive band (corresponding to the active auxiliary gene. 3. Elute the band containing the chromosomal fragment identified with the probe, and ligate the eluted DNA into a shuttle vector, such as pGC2. 4. Transform *E. coli* by selecting for the intact plasmid vector marker AmpR. 5. Probe transformants by colony hybridization, e.g., with the plasmid fragment probe. 6. Prepare plasmids and run on a gel. Identify the plasmids which are of larger size than the vector alone; these plasmids should have a size corresponding to the vector+insert. 7. Construct a physical map of the plasmid and compare it with the physical map of the plasmid containing the inactivated gene.

(C) Complementation assay. 1. The complementation assay involves the introduction of the recombinant plasmid putatively containing the inserted active allele of the auxiliary gene into the original aux mutant. The introduction of the recombinant vector can be attempted by electroporation (Luchansky et al., 1988, Mol. Microbio. 2:637–646), protoplast transformation (Chang and Cohen, 1979, Mol. Gen. Genet. 168:111–115), or prophage transformation (Pattee and Nevelin, 1975, J. Bacteriol. 124:201–211). The selection should be first for a plasmid marker, such as CmR (a plasmid pCG2 marker that is expressed in *S. aureus*), and then for methicillin resistance. If the complementation has worked fully, the phenotype of the transposon mutant carrying the shuttle vector with the aux gene should be the same as that of the original parent strain.

The step of cutting the chromosome of the parent strain can be simplified as follows: one class of mutants (located on the SmaI-A fragment) lie in the largest EcoRI fragment, of approximately 40 kb. This fragment can be easily resolved by PFGE electrophoresis from the other EcoRI fragments and eluted pure from the gel. The DNA of this 40 kb EcoRI fragment can then be cut with an appropriate restriction endonuclease as described in step B.2. The same simplification method can be applied to clone auxiliary genes that lie in the SmaI fragment I, and that lie in the largest HindIII fragment.

Generally, once the DNA fragments are generated, identification of the specific DNA fragment containing the desired auxiliary gene may be accomplished in a number of ways. For example, if an amount of a portion of an auxiliary gene or a fragment thereof is available and can be purified and labeled, the generated DNA fragments may be screened by nucleic acid hybridization to the labeled probe (Benton and Davis, 1977, Science 196:180; Grunstein and Hogness, 1975, Proc. Natl. Acad. Sci. U.S.A. 72:3961). Those DNA fragments with substantial homology to the probe will hybridize. The present invention provides specific examples of DNA fragments that can be used as hybridization probes for auxiliary genes, i.e., Tn551 mutants.

It is also possible to identify the appropriate fragment by restriction enzyme is digestion(s) and comparison of fragment sizes with those expected according to a known restriction map if such is available. Further selection can be carried out on the basis of the properties of the gene.

As described above, the presence of the gene may be detected by assays based on the physical, chemical, or immunological properties of its expressed product. For example DNA clones that produce a protein that, e.g., has similar or identical electrophoretic migration, isoelectric focusing behavior, proteolytic digestion maps, proteolytic activity, antigenic properties, or functional properties, especially cell wall synthetic activity, known for a particular auxiliary protein. In particular, DNA suspected of containing the auxiliary gene of interest can be introduced into a mutant bacterial strain, e.g., RUSA235 or RUSA168, to reconstitute normal phenotypic methicillin resistance, cell wall synthesis, and the like.

Alternatives to isolating the auxiliary genomic DNA include, but are not limited to, chemically synthesizing the gene sequence itself from a known sequence. For example, DNA cloning of an auxiliary gene can be isolated from Gram positive bacteria by PCR. Other methods are possible and within the scope of the invention.

The identified and isolated gene can then be inserted into an appropriate cloning vector. A large number of vector-host systems known in the art may be used. Possible vectors include, but are not limited to, plasmids or modified viruses, but the vector system must be compatible with the host cell used. For example, the auxiliary coding sequence can be inserted in an *E. coli* cloning vector. Other examples of vectors include, but are not limited to, bacteriophages such as lambda derivatives, or plasmids such as pBR322 derivatives or pUC plasmid derivatives, e.g., pGEX vectors, pmal-c, pFLAG, etc.

The insertion into a cloning vector can, for example, be accomplished by ligating the DNA fragment into a cloning vector which has complementary cohesive termini. However, if the complementary restriction sites used to fragment the DNA are not present in the cloning vector, the ends of the DNA molecules may be enzymatically modified. Alternatively, any site desired may be produced by ligating nucleotide sequences (linkers) onto the DNA termini; these ligated linkers may comprise specific chemically synthesized oligonucleotides encoding restriction endonuclease recognition sequences. Recombinant molecules can be introduced into host cells via transformation, transfection, infection, electroporation, etc., so that many copies of the gene sequence are generated.

In an alternative method, the desired gene may be identified and isolated after insertion into a suitable cloning vector in a "shot gun" approach. Enrichment for the desired gene, for example, by size fractionation, can be done before insertion into the cloning vector.

Alternatives to isolating the auxiliary genomic DNA include, but are not limited to, chemically synthesizing the gene sequence itself from a know sequence. For example, DNA cloning of an auxiliary gene can be isolated from Gram positive bacteria by PCR. Ohter methods are possible and within the scope of the invention.

In specific embodiments, transformation of host cells with recombinant DNA molecules that incorporate the isolated auxiliary gene or synthesized DNA sequence enables generation of multiple copies of the gene. Thus, the gene may be obtained in large quantities by growing transformants, isolating the recombinant DNA molecules from the transformants and, when necessary, retrieving the inserted gene from the isolated recombinant DNA.

The present invention also relates to vectors containing genes encoding analogs and derivatives of auxiliary proteins that have the same functional activity as an auxiliary proteins. The production and use of derivatives and analogs related to an auxiliary protein are within the scope of the present invention. In a specific embodiment, the derivative or analog is functionally active, i.e., capable of exhibiting one or more functional activities associated with a full-length, wild-type auxiliary protein.

In particular, derivatives can be made by altering encoding nucleic acid sequences by substitutions, additions or deletions that provide for functionally equivalent molecules. Due to the degeneracy of nucleotide coding sequences, other DNA sequences which encode substantially the same amino acid sequence as an auxiliary gene may be used in the practice of the present invention. These include but are not limited to nucleotide sequences comprising all or portions of auxiliary genes that are altered by the substitution of different codons that encode the same amino acid residue within the sequence, thus producing a silent change. Likewise, the derivatives of the invention include, but are not limited to, those containing, as a primary amino acid sequence, all or part of the amino acid sequence of an auxiliary protein including altered sequences in which functionally equivalent amino acid residues are substituted for residues within the sequence resulting in a conservative amino acid substitution For example, one or more amino acid residues within the sequence can be substituted by another amino acid of a similar polarity, which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid.

The genes encoding auxiliary protein derivatives and analogs of the invention can be produced by various methods known in the art. The manipulations which result in their production can occur at the gene or protein level. For example, a cloned auxiliary gene sequence can be modified by any of numerous strategies known in the art (Sambrook et al., 1989, supra). The sequence can be cleaved at appropriate sites with restriction endonuclease(s), followed by further enzymatic modification if desired, isolated, and ligated in vitro. In the production of the gene encoding a derivative or analog of an auxiliary protein, care should be taken to ensure that the modified gene remains within the same translational reading frame as the auxiliary gene, uninterrupted by translational stop signals, in the gene region where the desired activity is encoded.

Additionally, the auxiliary gene nucleic acid sequence can be mutated in vitro or in vivo, to create and/or destroy translation, initiation, and/or termination sequences, or to create variations in coding regions and/or form new restriction endonuclease sites or destroy preexisting ones, to facilitate further in vitro modification. Any technique for mutagenesis known in the art can be used, including but not limited to, in vitro site-directed mutagenesis (Hutchinson, C., et al., 1978, J. Biol. Chem. 253:6551; Zoller and Smith, 1984, DNA 3:479–488; Oliphant et al., 1986, Gene 44:177; Hutchinson et al., 1986, Proc. Natl. Acad. Sci. U.S.A. 83:710), use of TABS linkers (Pharmacia), etc. PCR techniques are preferred for site directed mutagenesis (see Higuchi, 1989, "Using PCR to Engineer DNA", in *PCR Technology: Principles and Applications for DNA Amplification*, H. Erlich, ed., Stockton Press, Chapter 6, pp. 61–70).

Once the gene is cloned, its sequence can be determined using any of the sequencing techniques known in the art.

Moreover, if desired, the gene can be expressed recombinantly, using the well known techniques for recombinant gene expression, in order to obtain a large sample of purified protein for structural and functional studies.

The gene coding for an auxiliary protein, or a functionally active fragment or other derivative thereof, can be inserted into an appropriate expression vector, i.e., a vector which contains the necessary elements for the transcription and translation of the inserted protein-coding sequence. An expression vector also preferably includes a replication origin. The necessary transcriptional and translational signals can also be supplied by the native auxiliary gene and/or its flanking regions. A variety of host-vector systems may be utilized to express the protein-coding sequence. Preferably, however, a bacterial expression system is used to provide for high level expression of the protein with a higher probability of the native conformation. Potential host-vector systems include but are not limited to bacteria transformed with bacteriophage, DNA, plasmid DNA, or cosmid DNA.

The expression elements of vectors vary in their strengths and specificities. Depending on the host-vector system utilized, any one of a number of suitable transcription and translation elements may be used.

Any of the methods previously described for the insertion of DNA fragments into a vector may be used to construct expression vectors containing a chimeric gene consisting of appropriate transcriptional/translational control signals and the protein coding sequences. These methods may include in vitro recombinant DNA and synthetic techniques and in vivo recombinants (genetic recombination).

Expression of nucleic acid sequence encoding an auxiliary protein or peptide fragment may be regulated by a second nucleic acid sequence so that the exported protein or peptide is expressed in a host transformed with the recombinant DNA molecule. For example, expression of an auxiliary protein may be controlled by any promoter/enhancer element known in the art, but these regulatory elements must be functional in the host selected for expression. For expression in bacteria, bacterial promoters are required ("Useful proteins from recombinant bacteria" in Scientific American, 1980, 242:74–94)

Expression vectors containing auxiliary gene inserts can be identified by four general approaches: (a) PCR amplification of the desired plasmid DNA or specific mRNA, (b) nucleic acid hybridization, (c) presence or absence of "marker" gene functions, and (d) expression of inserted sequences. In the first approach, the nucleic acids can be amplified by PCR with incorporation of radionucleotides or stained with ethidium bromide to provide for detection of the amplified product. In the second approach, the presence of a foreign gene inserted in an expression vector can be detected by nucleic acid hybridization using probes comprising sequences that are homologous to an inserted gene. In the third approach, the recombinant vector/host system can be identified and selected based upon the presence or absence of certain "marker" gene functions (e.g., β-galactosidase activity, PhoA activity, thymidine kinase activity, resistance to antibiotics, transformation phenotype, occlusion body formation in baculovirus, etc.) caused by the insertion of foreign genes in the vector. If the auxiliary gene is inserted within the marker gene sequence of the vector, recombinants containing the insert can be identified by the absence of the marker gene function. In the fourth approach, recombinant expression vectors can be identified by assaying for the activity of the gene product expressed by the recombinant. Such assays can be based, for example, on the physical or functional properties of the auxiliary gene product in suitable assay systems, e.g., cell wall synthesis.

Once a suitable host system and growth conditions are established, recombinant expression vectors can be propagated and prepared in quantity.

In addition, a host cell strain may be chosen which modulates the expression of the inserted sequences, or modifies and processes the gene product in the specific fashion desired. Expression from certain promoters can be elevated in the presence of certain inducers; thus, expression of the genetically engineered auxiliary protein may be controlled. Furthermore, different host cells have characteristic and specific mechanisms for the translational and post-translational processing and modification (e.g., cleavage of signal sequence) of proteins. Appropriate cell lines or host systems can be chosen to ensure the desired modification and processing of the foreign protein expressed. Different vector/host expression systems may effect processing reactions, such as proteolytic cleavages, to a different extent.

Biochemical Activity of Auxiliary Proteins

Generally, the invention provides for identification of a functional property of a protein produced by an auxiliary gene by comparing the homology of the deduced amino acid or nucleotide sequence to the amino acid sequence of a known protein, or the nucleotide sequence of the gene encoding the protein.

An important aspect of the invention is ability to characterize the biochemical activity of the protein encoded by the auxiliary gene, particularly the auxiliary genes of mutant RUSA168, by biochemical and phenotypic analysis. Information about the biochemical activity of the protein provides direction for identifying antagonists, as described below.

Transposon inactivation experiments indicate that the functioning of the mecA gene and auxiliary genes are both essential for the expression of high level methicillin resistance. Although not intending to be limited by any particular theory, a conceivable model would be as follows. As the β-lactam antibiotic level begins to increase in the environment of the bacteria, the antibiotic molecules penetrate the cell surface and inactivate (by covalent bond formation) the normal complement of the four staphylococcal PBPs which have relatively high affinities for the drug molecules. In vitro experiments indicate that within the methicillin concentration range of 5 to 10 mg/L, all four "normal" PBPs become fully acylated. One may assume that under these conditions, perhaps upon the generation of a cellular signal, the low affinity PBP2A takes over the task of cell wall synthesis. It was shown that in the highly resistant strain COL (methicillin MIC=1600 mg/L), addition of 5–10 mg/L methicillin to the medium resulted in a striking change in the composition of peptidoglycan (de Jonge and Tomasz, 1993, Antimicrobial. Agents and Chemotherapy, 37:342–6). In drug free medium, this bacterium produces a cell wall composed of a diverse family of over 35 muropeptide components, the majority (60%) of which are trimers or higher oligomers of muropeptides. When grown in the methicillin containing medium, this complex wall structure is replaced by a simple one in which the peptidoglycan is made up of essentially two components; the pentaglycyl monomer and its dimer, with only a very small amount of trimers and traces of higher oligomers. Bacteria continue to produce this simple peptidoglycan throughout a vast range of antibiotic concentrations in the medium for 5 mg/L (<0.1% of the MIC) up to 750 mg/L (½×the MIC). The observations suggest that at the critical concentration of about 5 mg/L methicillin, a new cell wall synthetic machinery, presumably PBP2A, takes over. In this model, PBP2A is assumed to be a peculiar transpeptidase which can only link two monomers together, but is incapable of generating the highly crosslinked oligomers which are the characteristic products of the normal wall synthetic machinery (de Jonge and Tomasz, 1993 supra). It may be that blocks in the synthesis of "normal" muropeptides (i.e., inactivation of auxiliary genes) can cause such striking reductions in the effectiveness of this resistance mechanism (i.e., decrease in the MIC from 1600 to 3 mg methicillin per liter) in spite of the presence of large amounts of PBP2A because effective functioning of PBP2A also requires an abundant supply of structurally correct cell wall building blocks. The correct building blocks may successfully compete with the methicillin molecules for the active site of PBP2A. Muropeptides of "incorrect" structure (e.g., less than five glycine units in the crosslinking peptides, or lack of amidation of the glutamic residues) compete less effectively with the antibiotic molecule, which translates to a decrease in the methicillin MIC value (see FIG. 1A and B).

The role of auxiliary proteins in cell wall synthesis can be indirectly evaluated by analyzing the composition of the cell wall.

Figure 2:
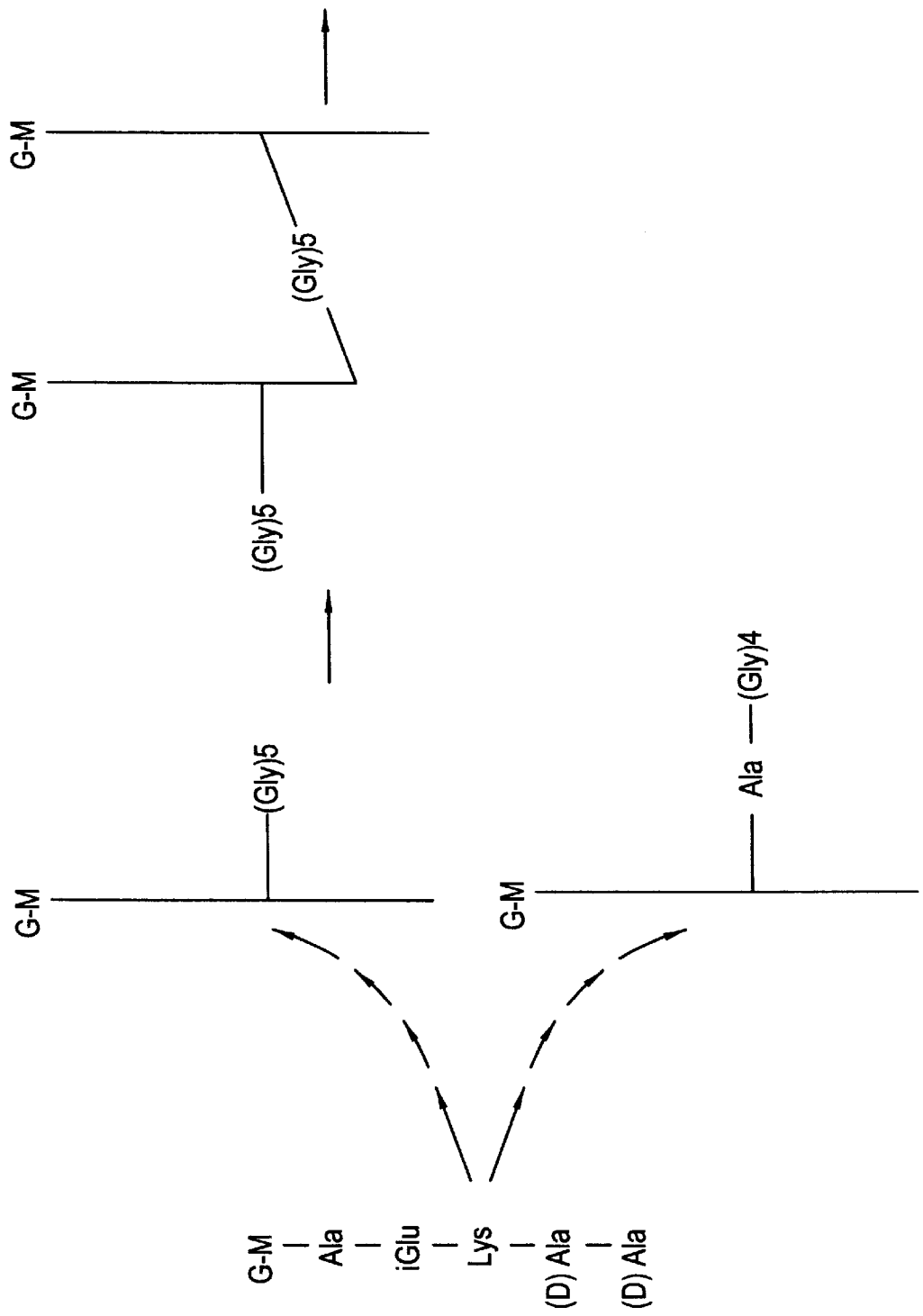
FIG. 2. Suggested pathway for the addition of crosslinking peptides to the pentapeptide precursors. Symbols: G—N-acetylglucosamine; M—N-acetylmuramic acid; Ala, iGlu, Lys—alanine, isoglutamine and lysis, respectively. The synthetic pathway is interrupted at various steps in the auxiliary mutants.

Cell wall peptidoglycan can be prepared from parental strains and from mutants. The muropeptide building blocks of the peptidoglycan (liberated by enzymatic digestion) can be separated by reverse phase high performance liquid chromatography (HPLC) (de Jonge et al., 1992, J. Biol. Chem. 267:11248–54). Inactivation of the mecA gene causes no detectable change in muropeptide composition. Inactivation of auxiliary genes may cause major and unique composition changes in the peptidoglycans, which can be identified by differences in HPLC elution profiles of muropeptides isolated from enzymatic cell wall peptidoglycan hydrolysates of a parental strain and of mutants (See e.g., de Jonge et al., J. Bacteriol. 173:1105–10; de Jonge et al., 1992, J. Biol. Chem. 269:11255–9; Maidhof et al., 1991, J. Bacteriol. 173:3507–13; de Jonge et al., 1993, J. Bacteriol. 175:2779–82). These unique wall composition changes may be reproduced with precision. The results can indicate, e.g., that auxiliary genes control the biosynthesis of the oligopeptide substituent on the epsilon amino group of the lysine residue in the muropeptide stem in staphylococci (FIG. 2).

In a specific embodiment, infra, mutation to a staphylococcal auxiliary gene results in a partial block in the cytoplasmic peptidoglycan precursor synthesis of the pentapeptide at the addition of the third (lysine) residue. This block is reflected in the appearance of two new monomeric muropeptides in the cell wall of the mutant strain, and the presence of large amounts of a component in the precursor pool with retention time characteristic of a dipeptide. This component that builds up in the precursor pool is not present in parental cells.

In parental strains COL and M100, the most abundant monomer is the disaccharide pentapeptide substituted with a pentaglycyl unit on the epsilon amino group of the lysine residue, and this monomer is also the major building block of dimers, trimers and higher oligomers of the peptidoglycan.

Various muropeptide alterations may be observed. For example, synthetic blocks can occur at a step past addition of a fourth glycine; at a step past the addition of a first glycine; in the synthesis of minor muropeptides; in the synthesis of peptidoglycans; or in the amidation of the x-carboxyl group of the stem peptide glutamic acid residues (see de Lencastre et al., 1994 "Molecular Aspects of Methicillin Resistance in *Staphylococcus aureus*", J. Antimicrob. Chemother. 33; de Jonge et al., 1992, J. Biol. Chem. 267:11255–9; Ornelas-Soares et al., 1993, J. Biol. Chem. 268:26268–72).

Auxiliary Gene and Protein Antagonists

Although bacterial mutation can be used to identify genes associated with antibiotic resistance, random mutagenesis to knock out auxiliary genes is not a therapeutically attractive treatment regimen for bacterial, in particular, staphylococcal, infection. Thus, the present invention contemplates inactivation of auxiliary genes and proteins, in particular the gene having a nucleotide sequence set forth in FIG. 11 (SEQ ID NO:1) and protein encoded thereby, using compounds that antagonize the activity of the protein, or with antisense nucleic acids to inhibit expression of the protein. The activity for the protein encoded by the gene having a nucleotide sequence set forth in FIG. 11 (SEQ ID NO:1) may be related to that of the σ-factor that is involved with the stress response in *B. subtilis*, because of its strong homology thereto.

In one embodiment, antisense nucleic acids that are complementary to the auxiliary gene mRNA can be administered to a subject suffering from a bacterial infection. Such nucleic acids can be DNA or RNA, preferably DNA, and more preferably DNA containing non-phosphate bonds, and thus is resistant to nuclease degradation in vivo.

As noted above, according to one non-binding theory of the invention, the suppression of antibiotic resistance by inactivation of these genes must be caused by the block in the production of the corresponding gene products that are essential for the phenotypic expression of resistance. Specific antagonists of these gene products can be screened for use as chemical agents capable of re-sensitizing the bacteria to beta lactam antibiotics.

One way for searching for such compounds would involve incorporating candidates into test systems containing appropriate concentrations of the beta lactam antibiotics and the test organisms, e.g., the highly methicillin resistant strain of *S. aureus*, strain COL. Effective compounds would be expected to reduce methicillin resistance at sub-inhibitory levels.

In another embodiment, screening for active compounds is based on observing similar or identical phenotypic changes in the antibiotic resistant bacteria, e.g., cell wall composition, accumulation of muramyl peptides, and the like, in the bacteria in the presence of a candidate inhibitor.

In a specific embodiment, the invention provides inhibitors of the step of addition of lysine to the muramyldipeptides alanylglutamate and alanalyisoglutamine. Such inhibitors may be selected from the group consisting of but not limited to analogs of isoglutamine, analogs of glutamic acid, analogs of UDP-N-acetylmuramylalanylglutamate, analogs of UDP-N-acetylmuramylalanylisoglutamine, and analogs of lysine. Such analogs are characterized by having the same topological structure, and therefore the same recognition features, as the natural precursors, but are modified to be non-reactive, thus competitively inhibiting the auxiliary gene product and thereby reducing methicillin resistance.

Any screening technique known in the art can be used to screen for suitable auxiliary protein antagonists. For example, bacterial phage or synthetic random libraries, e.g., preferably encoded synthetic libraries (Needels et al., 1993, "Generation and screening of an oligonucleotide encoded synthetic peptide library," Proc. Natl. Acad. Sci. USA 90:10700–4; Lam et al., International Patent Publication No. WO 92/00091, published Jan. 9, 1992) can be used.

The screening can be performed with bacteria, or alternatively, using purified protein, e.g., produced recombinantly, as described above.

Knowledge of the primary sequence of the protein, and the similarity of that sequence with proteins of known function, can provide an initial clue as the inhibitors or antagonists of the protein. Identification and screening of antagonists is further facilitated by determining structural features of the protein, e.g., using X-ray crystallography, neutron diffraction, nuclear magnetic resonance spectrometry, and other techniques for structure determination. These techniques provide for the rational design or identification of inhibitors and antagonists.

In a specific embodiment, a preliminary screen was performed in which several "early" cell wall inhibitors were shown to mimic the effect of auxiliary mutations when added to the methicillin containing medium at sub-inhibitory concentrations of D-cycloserine and fosfonomycin.

Treatment of Antibiotic Resistant Bacterial Infections

The present invention provides methods and compositions for the treatment of infections with antibiotic resistant or multiple antibiotic resistant bacteria. In its primary aspect, the invention provides for co-administration of a compound that inhibits or antagonizes an auxiliary protein involved in cell wall synthesis in conjunction with an antibiotic or antibiotics to which the bacterium is normally resistant.

Accordingly, the invention provides pharmaceutical compositions comprising a compound that antagonizes an auxiliary protein in an amount effective to antagonize the activity of an auxiliary protein, and a pharmaceutically acceptable carrier. In another embodiment, the pharmaceutical composition further comprises an antibiotic in an amount effective to treat a bacterial infection.

Preferably, the antibiotic is any member of the beta lactam family of antibiotics. In a specific aspect, the antibiotic is methicillin.

A particularly attractive feature of this strategy is that it does not involve the search for new antibiotic agents but rather it proposes to find agents that bring the target bacterium back to within the inhibitory range of well characterized antibiotics such as beta lactams.

This strategy is also applicable for the selection of agents that could resensitize bacteria to other types of antibiotics also. In addition, agents capable of sensitization to methicillin may very well be active in a similar manner in beta lactam resistant strains of other bacterial species such as *Enterococcus faceium* and *E. faecalis*, penicillin resistant pneumococci ($pen^R$ pneumococci), and coagulase-negative staphylococci.

According to the present invention, the therapeutic compositions and methods of the invention can be used to protect an animal subject from infection of a Gram positive bacteria. Thus, a therapeutic composition or method of the invention can be used in birds, such as chickens, turkeys, and pets; and in mammals, preferably humans, as well as other mammalian species, including but not limited to domesticated animals (canine and feline), farm animals (bovine, ovine, equine, caprine, porcine, and the like), rodents, and undomesticated animals.

The present invention will be better understood from a review of the following illustrative description.

EXAMPLE 1

Reassessment of the Number of Auxiliary Genes Essential for the Expression of High Level Methicillin Resistance in *Staphylococcus aureus*

A new transposon library constructed in the background of the highly and homogeneously methicillin resistant *Staphylococcus aureus* (MRSA) strain COL yielded 70 independent insertional mutants with reduced levels of antibiotic resistance. Southern hybridization with a Tn551 probe localized the inserts in 7 out of the 16 SmaI chromosomal fragments (fragments A,B,C,D,E,F, and I). Further restriction analysis with HindIII, EcoRV, EcoRI and PstI demonstrated that 58 of the 70 Tn551 mutants represented novel, as yet undescribed insertion sites. In all of the auxiliary mutants, expression of methicillin resistance became heterogeneous and the minimal inhibitory concentration (MIC) of the majority of cells was reduced to 1.5 μg up to 200 μg/ml from the homogeneous methicillin MIC of 1600 μg/ml in the parental cell. The findings indicate that a surprisingly large number of staphylococcal genes, in addition to mecA, are needed for the optimal expression of antibiotic resistance.

Materials and Methods

Strains and growth conditions. The *S. aureus* reference strains used are listed in Table 1 and were grown as described before (18). Transposon mutants and their backcrosses were also grown as previously described (18).

Selection of Tn551 mutants. The transposition experiment and selection of mutants was carried out by a modification of a previously described method (19). The parent strain COL harboring the thermosensitive plasmid pRN3208 carrying Tn551 with the erythromycin resistance determinant (referred to as COL [pRN3208])) was grown overnight at 30° C, and then diluted and plated at different cell concentrations on TSA (tryptic soy agar; Difco) containing 20 μg of erythromycin per ml. Plates were incubated at 30° C. and 43° C. for 48 hours. The approximate frequency of transposition (number of colonies at 43° C./number of colonies at 30° C.) was $2.1\cdot10^{-5}$. The erythromycin resistant colonies were checked for cadmium resistance (0.25 mM $CdNO_3$). The colonies that were cadmium resistant (indicating the integration of the whole plasmid) were grown on TSA at 43° C. for 16 hours to eliminate the plasmid, and tested again for cadmium resistance. Only colonies that were erythromycin resistant-cadmium sensitive were kept for further study. Each selected colony was grown on TSA containing 10 μg ml$^{-1}$ erythromycin and used to screen for decreased methicillin resistance.

Screening of mutants with decreased methicillin resistance. The erythromycin resistant (ery$^R$) colonies were tested sequentially by three screens.

In the first screen, all ery$^R$ colonies were streaked on plates with erythromycin (10 μg ml$^{-1}$) and different concentrations of methicillin (0; 25; 50 and 400 μg ml$^{-1}$); three controls were used in the same plates—RUSA10, RUSA12F and COL (pRN3208). We identified as putative mutants all colonies that failed to grow in any of the media with methicillin, using COL (pRN3208) as the positive control. In the second screen, the colonies identified in the previous screen as affected in resistance were grown overnight in 5 ml tryptic soy broth (TSB) with 10 μg ml$^{-1}$ erythromycin, and then tested on TSA plates containing a 1 mg methicillin disc. The controls referred to above were tested under the same conditions. After 24 hours of incubation at 37° C., the halos of inhibition were measured. The strains that gave inhibition halos larger that the ones of COL (pRN3208) were studied by a third screen.

In the third screen the colonies were analyzed by population analysis profiles (PAPs). We kept for further study the colonies that showed a PAP profile different from the one of COL (pRN3208): all the 70 selected mutants selected in this manner had MICs (minimal inhibitory concentration) lower than the one of the parent strain and all but two mutants also showed heterogeneous methicillin resistance phenotypes.

Population analysis profiles were performed as described (8) on plates containing methicillin (0, 1.5, 3, 6, 12.5, 25, 50, 100, 200, 400, and 800 μg/ml). Mutants 10 were assigned to different expression classes according to a previous classification (Tomasz et al., 1991, Antimicrob. Agents Chemother. 35:124–129), with the addition of an intermediate class, class 2-3. The critical parameter for the assignment of a PAP to a particular class was the MIC for the majority of the cells, as follows: class 1, 1.5 to 3 μml$^{-1}$; class 2, 6 to 12 μg l$^{-1}$; class 2–3, 25 to 50 μg ml$^{-1}$; class 3, 100 to 200 μg ml$^{-1}$; class 4, greater than 400 μg ml$^{-1}$; RUSA4 type (mecA::Tn155), 3 μg ml$^{-1}$. Strains of classes 1 to 3 are heterogeneous, whereas strains of class 4 or of the RUSA4 type are homogeneous.

Transduction crosses. Transduction crosses using the newly isolated mutants as donors and the homogeneously resistant strain COL as recipient, were performed with phage 80 alpha, as described (18). The primary selection was for the transposon marker erythromycin (10 μg/ml). A total of 50 to 100 ery$^R$ transductants from each transduction were streaked onto TSA plates containing erythromycin (10 μg ml$^{-1}$) and erythromycin plus methicillin (10 μg/ml and 400 μg/ml, respectively) by using positive and negative controls COL(pRN3208) and the particular donor strain used in the cross, respectively. All erythromycin-resistant transductants were found to show reduced levels of methicillin resistance as well. From each cross, eight transductants were further tested for decreased levels of methicillin resistance by the 1-mg methicillin disc method, and two ro three transductants were also tested by PAP analysis for their antibiotic resistance phenotypes. The locatio of the insert was tested by comparing the HindIII hybridization patterns of transductants and their donors.

Conventional and pulsed-field gel electrophoresis. Preparation of chromosomal DNA for conventional and pulsed-field gel electrophoresis (PFGE) was performed as previously published (10). Restriction digestions with SmaI, EcoRI, EcoRV, PstI and HindIII nucleases were carried out according to the manufacturer's recommendations. Conventional gel electrophoresis in 1% agarose in was carried out in 1×TAE buffer (21), for 16 h at 30–38 volts.

For pulsed-field gel electrophoresis, the gels were prepared with 1. 1% agarose (SeaKem LE, FMC Bioproducts) in 0.5×TBE buffer as previously described (10). The gels were run in an LKB 2015 Pulsaphor System (Pharmacia) or in a Chef-DR II apparatus (Bio-Rad). The running conditions for the SmaI restriction digests were as previously described (10). Chromosomal fragments higher than 15 kb (which are difficult to separate by conventional gel electrophoresis) were run in a Chef-DR II apparatus (Bio-Rad, USA) for 23 h at 14° C. in the same buffer. The running conditions were as follows: the voltage was set at 200 V, ramped with initial forward time 0.5 sec, final forward time 1.5 sec.

DNA transfer. For blotting of normal gels to nitrocellulose membranes (Schleicher & Schuell BA85, USA) a vacuum blotting apparatus was used (Vaccu-blot, Pharmacia/LKB) according to the manufacturer's instructions. For the blotting of pulsed-field gel electrophoresis gels we followed a previously described method (10).

Preparation of DNA probes and hybridization. The whole plasmid pRT1 (that contains an internal fragment of the transposon Tn551) was used as probe. pRT1 contains a 4 kb HpaI-XbaI fragment from the transposon Tn551 cloned in the SmaI site of the plasmid pGEM. 1 (Promega). Standard methodology was followed for $^{32}$P labeling of the probes by nick translation, prehybridization and hybridization (20). The hybridization was carried out at 42° C. in 50% formaldehyde. Nick translated plasmid DNA was denatured and added to hybridizations without separation of unincorporated nucleotides. When the membranes were rehybridized, the previous probe was removed by boiling in 0.1% SDS for 10 min. To ascertain the location of insertions the femA-femB region plasmids pGC42 and pBBB31 containing the 2.2 EcoRV and a 10.5 kb PstI fragment, respectively, were used (2).

Physical characterization of the mutants with EcoRI, PstI, EcoRV, and HindIII by probing with the Tn551probe. The enzymes EcoRI, PstI, and EcoRV have no restriction sites in Tn551, whereas the enzyme HindIII has two recognition sites (21), both of which are included in the probe used. The sizes of the DNA fragment generated after restriction enzyme digestion with EcoRI, PstI, and EcoRV and hybridization with the Tn551 probe represent the sum of the chromosomal fragment size, in which the transposon is integrated with the size of Tn551 (5.2 kb). In Tables 2 to 5, the molecular sizes of the fragments are given after subtraction of 5.2 kb. Hybridization of the DNAs restr4icted with HindIII generates three bands: one corresponds to the internal Tn551-HindIII fragment, and there are two others (one includes the 1.0 -kb HindIII-Tn551 right junction and the other includes the 3.0-kb HindIII-Tn551 left junction). As with the other enzymes, the results presented in Tables 2 to 5 indicate the size of the fragments in which insertions were located (i.e., the sum of the three hybridization bands minus 5.2 kb). HindIII was found to be the most useful enzyme for ascertaining the identity of two different insertions and was used to identify the number of different insertion sites in the new transposon library.

Results

Isolation of the Tn551 mutants with reduced methicillin resistance. By transposition of Tn551 into the chromosome of the homogeneously resistant strain COL, 1012 erythromycin resistant colonies were obtained. Seventy out of these 1012 colonies showed, by population analysis profiles, a decrease in methicillin resistance compared with the parent strains COL or COL (pRN3208). Moreover, in all but two of the mutants, the Tn551 insertion changed the phenotypic expression of resistance from homogeneous to heterogeneous. Among the 70 mutants a wide range of methicillin MICs were found, from strains with an MIC as low as 1.5 $\mu$g ml$^{-1}$ to strains with an MIC as high as 200 $\mu$g ml$^{-1}$ (see data in Tables 2 through 6). The locations of the Tn551 inserts relative to those of the already characterized femA, femB, femC, and femD genes were determined by physical mapping in order to identify how many of the mutants had novel insertion sites, possibly in new genes.

Figure 3A:
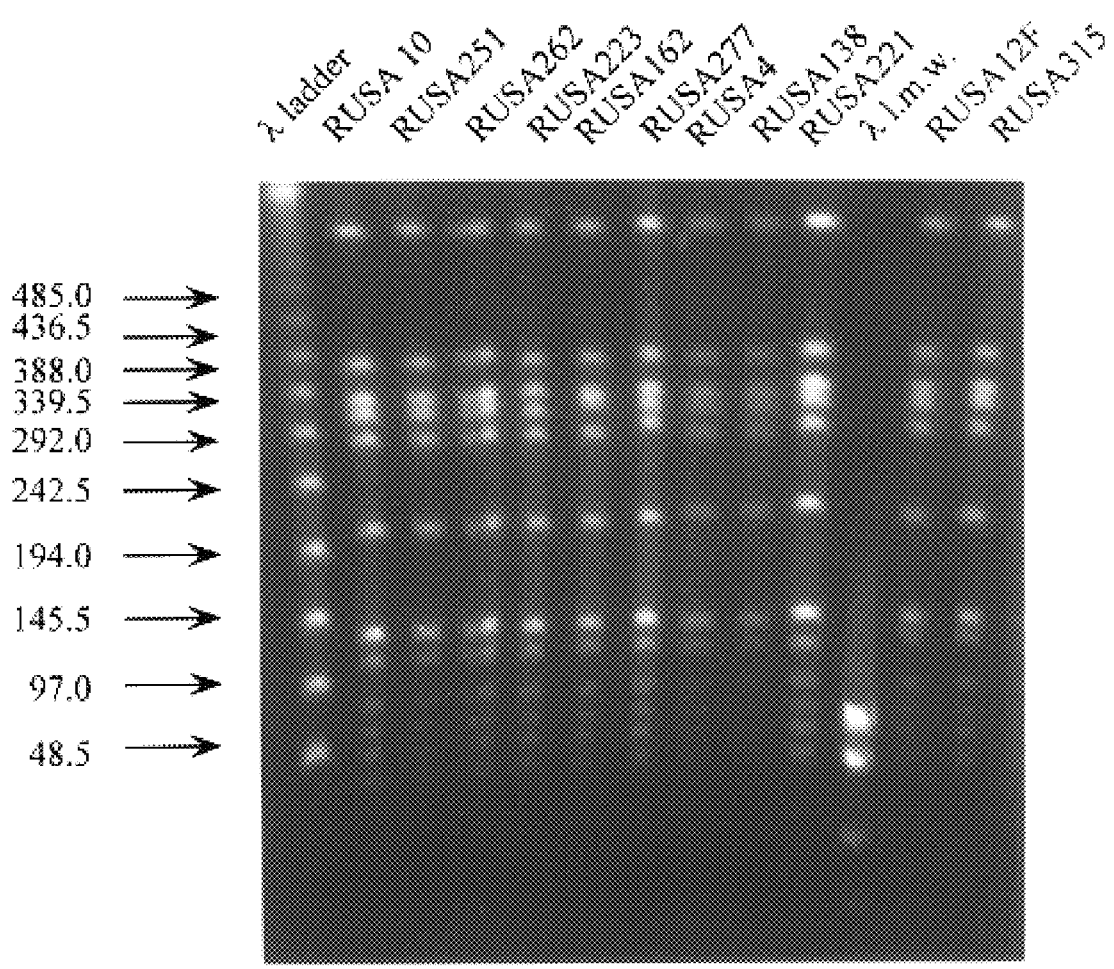
FIGS. 3A and 3B. Localization of Tn551 inserts in chromosomal SmaI fragments by Southern hybridization. Chromosomal DNA prepared from a selected group of Tn551 mutants was treated with SmaI endonuclease and the fragments were separated by pulsed-field gel electrophoresis (FIG. 3A). After transfer of the DNA, membranes were hybridized by a radiolabeled Tn551 DNA probe, as described in the Methods (FIG. 3B).
Figure 3B:
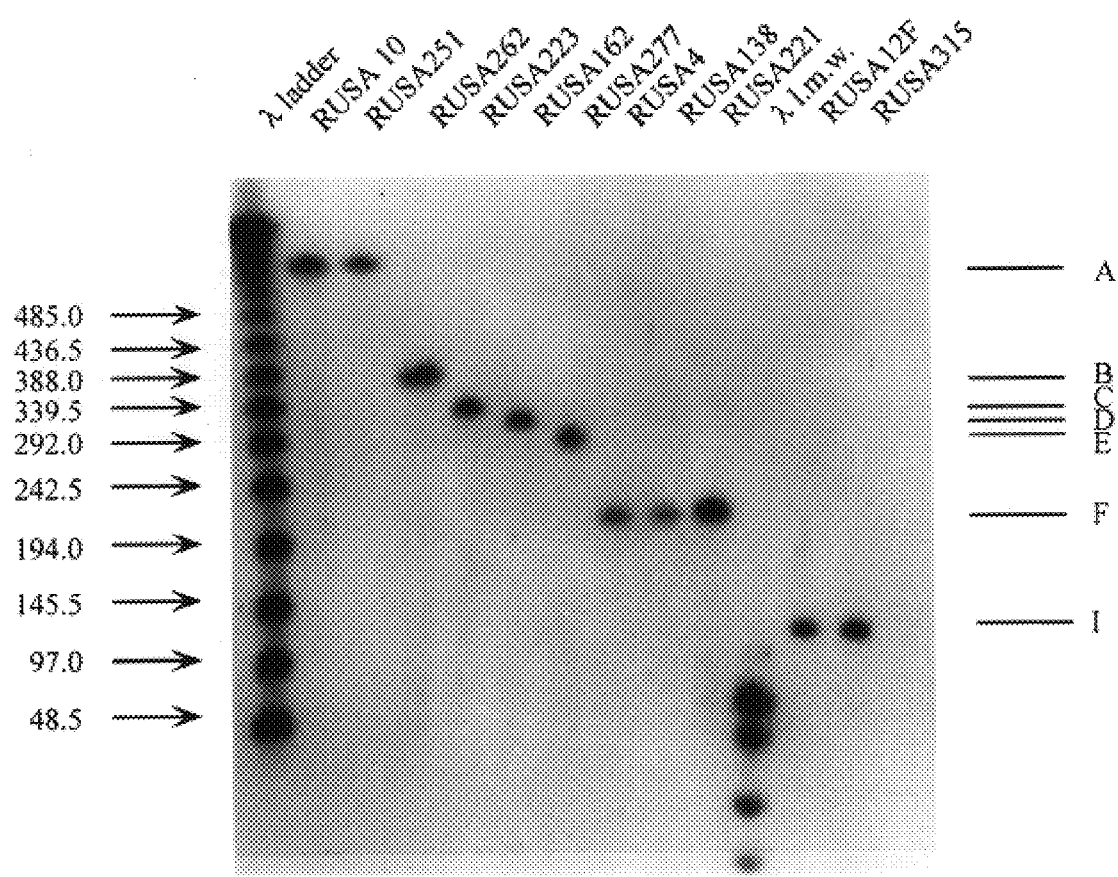

Physical location of the Tn551 inserts in the staphylococcal chromosome. The Tn551 inserts of the 70 independently selected mutants were mapped in the staphylococcal chromosome. The DNA of each mutant was restricted with the SmaI restriction endonuclease and then separated by pulsed-field gel electrophoresis. After photography under the UV, the DNA fragments were transferred to a membrane and hybridized with the Tn551 labeled probe. Tn551 insertions were located in seven out of the 16 fragments obtained by restriction of the *S. aureus* chromosome with SmaI. The distribution of the 70 mutants among the fragments was the following: SmaI-A, 48; SmaI-B, 4; SmaI-C, 1; SmaI-D, 1; SmaI-E, 2; SmaI-F, 3; and SmaI-I, 11. In FIGS. 3A and 3B the location of representative mutations in the seven SmaI fragments is shown.

Physical characterization of the Tn551 mutants located on the various SmaI chromosomal fragments. The DNAs of the mutants were digested with the appropriate restriction endonuclease, separated by conventional gel electrophoresis (or PFGE for fragments >15 kb) and hybridized with a Tn551 specific probe (pRT1). In some cases, after removing the Tn551 probe, the same DNAs were hybridized with a femA probe (pBBB31) or with a femA-femB probe (pBBB13).

Mutants in fragment SmaI-A. The previously studied Tn515 mutants in the femA, femB, and femC genes map in the SmaI fragment A (4). In order to compare the new mutants with the previously characterized ones, DNAs of the 48 new mutants that map in fragment SmaI-A (see Table I) were restricted with EcoRI, an enzyme that has no restriction sites in Tn551.

TABLE 1

Reference strains used in the study

| Strain | Relevant genotype | Relevant phenotype | PAP expression class | MIC ($\mu$g ml$^{-1}$) | Origin or reference |
|---|---|---|---|---|---|
| Parental | | | | | |
| COL | — | Homogeneous Mc$^r$ | 4 | 1,600 | RU collection |
| COL (pRN3208) | COL with pRN3208 [Rep(Ts)] | Mc$^r$ Em$^r$ Cd$^r$ | 4 | 800 | 15 |
| M100 | Laboratory step mutant of strain 27s | Homogeneous | | 25 | 9, 25 |
| Tn551 mutants of COL Mapped in SmaI-A | | | | | |
| BR403 | COL Ω2003 (femA::Tn551) | Em$^r$ heterogeneous Mc$^r$ | 2–3 | 25[a] | 1, 2 |
| RUSAIII-8 | COL Ω560 (femA::Tn551) | Em$^r$ heterogeneous Mc$^r$ | 2 | 12 | 2, 9, 15 |
| RUSA10 | COL Ω552 (femB::Tn551) | Em$^r$ heterogeneous Mc$^r$ | 1 | 3 | K. Murakami; 9 |
| RUSAIII-3 | COL Ω553 (femB::Tn551) | Em$^r$ heterogeneous Mc$^r$ | 1 | 3 | J. Kornblum; 9 |
| RUSA1H1 | COL Ω554 (femB::Tn551) | Em$^r$ heterogeneous Mc$^r$ | 1 | 3 | J. Kornblum; 9 |
| RUSA20F | COL Ω555 (femB::Tn551) | Em$^r$ heterogeneous Mc$^r$ | 1 | 3 | J. Kornblum; 9 |
| RUSAIII-2 | COL Ω556 (femB::Tn551) | Em$^r$ heterogeneous Mc$^r$ | 1 | 3 | 2, 9, 15 |
| RUSAII-1 | COL Ω557 (femB::Tn551) | Em$^r$ heterogeneous Mc$^r$ | 1 | 3 | 2, 9, 15 |
| RUSA208[b] | COL Ω561 (femC::Tn551) | Em$^r$ heterogeneous Mc$^r$ | 1 | 3 | 18 |
| RUSA330 (1H)[c] | COL Ω2005 (femC::Tn551) | Em$^r$ heterogeneous Mc$^r$ | 1 | 3 | 4, 15 |
| RUSA101 | COL Ω559 (femE::Tn551) | Em$^r$ heterogeneous Mc$^r$ | 2–3 | 12–25 | 9 |
| Mapped in SmaI-F, RUSA4 | COL Ω551 (mecA::Tn551) | Em$^r$ reduced Mc$^r$ | RUSA4 type | 3 | 9, 16, 17 |

TABLE 1-continued

Reference strains used in the study

| Strain | Relevant genotype | Relevant phenotype | PAP expression class | MIC ($\mu$g ml$^{-1}$) | Origin or reference |
|---|---|---|---|---|---|
| Mapped in SmaI-I, RUSA12F | COL Ω558 (femD::Tn551) | Em$^r$ heterogeneous Mc$^r$ | 2 | 12 | 4, 15 |

[a]The MIC for COL derivatives with the mutation Ω2003 is greater than the one for the original mutant in the BB270 background (1).
[b]Ten other mutants (Ω562 to Ω571) have the same restriction pattern as strain RUSA208 (Ω561) (18).
[c]This strain was obtained by transduction of the insert from mutant 1H (Ω2005) (15) into strain COL from the RU collection.

We found that the 48 new mutants could be divided in two groups according to their restriction with EcoRI. The 48 mutants were further studied by restriction analysis with PstI, EcoRV, and HindIII, enzymes used to characterize the original femA, femB and femC mutants (2, 4, 11).

Figure 4:
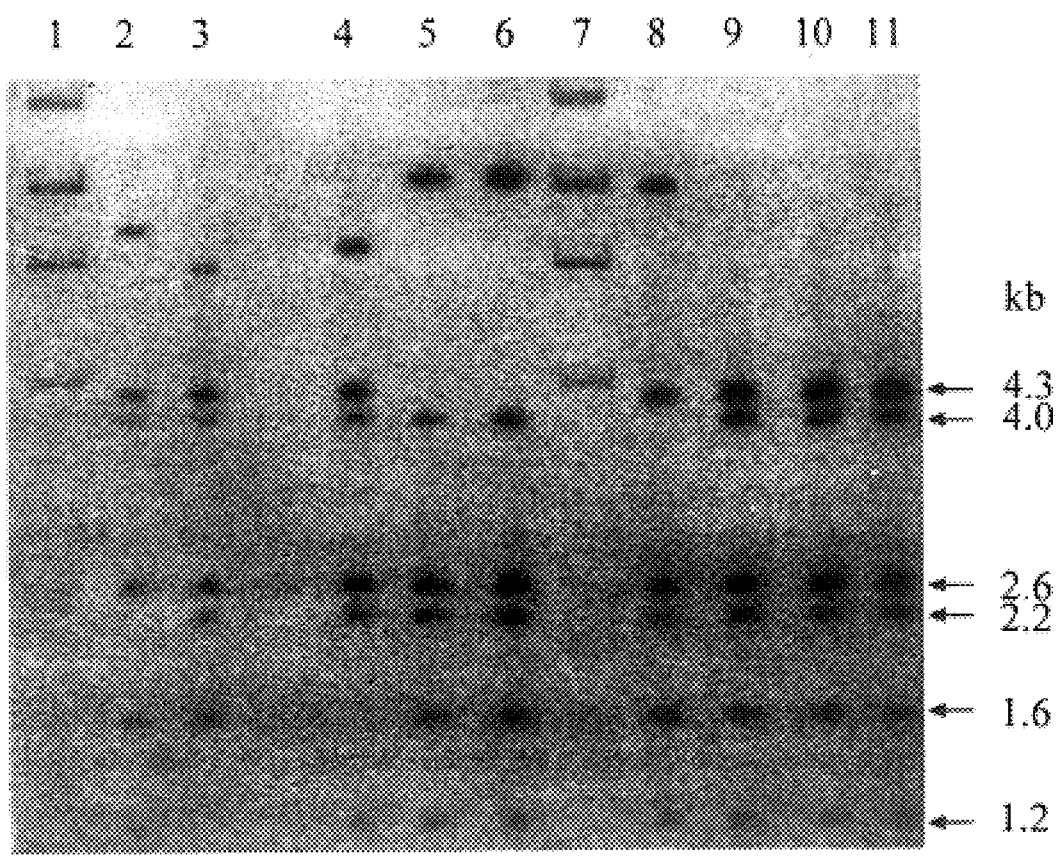
FIG. 4. Southern blots of EcoRV restriction digests of mutants located in EcoRI-a. Mutant DNA was digested with EcoRV and probed with the 10.5 kb PstI fragment from plasmid PBBB13 covering the femA-femB region (2). Lanes: 1 and 7, bacteriophage lambda plus HindIII; 2, strain BB403 (femA::Tn551); 3, strain RUSA251; 4, strain RUSA148; 5, strain RUSA270; 6, strain RUSA217a; 8, strain RUSA291; 9, strain RUSA252; 10, strain RUSA101; 11, strain RUSA279.

The first group includes 11 mutants (Table 2) mapping in the largest EcoRI fragment of approximately 40 kb (EcoRI-a), where the femA and femB genes are also located (2).

lar size of which corresponded to that of the lost fragment plus the size of Tn551 (5.2 kb). For instance, in mutant RUSA251 the 1.2 kb band was replaced by a 6.4 kb band; in RUSA148 the 1.6 kb band was replaced by a 6.8 kb band; in RUSA291 the 4.0 kb band was replaced by a 9.2 kb band; and in mutants RUSA270 and RUSA217a, the 4.3 kb band was replaced by a 9.5 kb band (FIG. 4).

Next, these five mutants were further characterized by HindIII restriction. The insert in mutant RUSA251 was

TABLE 2

New Tn551 mutants with mutations mapping in EcoRI fragment a

| Strain | Ω no. | Size of restriction fragment (kb) | | | PAP expression class | MIC ($\mu$g ml$^{-1}$) | Backcross |
|---|---|---|---|---|---|---|---|
| | | PstI | EcoRV | HindIII | | | |
| RUSA251 | COL Ω573 | α = 10.5 | 1.2 | 5.4 | 1 | 3 | RUSA251 |
| RUSA148 | COL Ω574 | α = 10.5 | 1.6 | 6.8 | 2–3 | 25 | RUSA148 |
| RUSA270 | COL Ω575 | α = 10.5 | 4.3 | 2.2 | 2–3 | 25 | RUSA270 |
| RUSA291 | COL Ω576 | α = 10.5 | 4.0 | 7.3 | 2–3 | 25 | |
| RUSA217a | | α = 10.5 | 4.3 | —* | 2–3 | 25 | |
| RUSA101 | COL Ω559 | β = 12.4 | 2.5 | 2.9 | 2–3 | 25 | RUSA101 |
| RUSA321 | COL Ω577 | β = 12.4 | 2.5 | 2.9 | 2–3 | 25 | RUSA321 |
| RUSA252 | COL Ω579 | β = 12.4 | 0.5 | 7.3 | 3 | 100 | RUSA252 |
| RUSA279 | COL Ω580 | β = 12.4 | 2.5 | 2.4 | 3 | 50 | RUSA279 |
| RUSA289 | COL Ω581 | β = 12.4 | 7.8 | 10.1 | 3 | 100 | |
| RUSA301 | COL Ω582 | β = 12.4 | 5.9 | 11.6 | 2–3 | 25 | |

*—, only two HindIII fragments were visible after hybridization with the Tn551 probe; the fragment containing the Tn551 right junction is missing.

The 11 mutants whose inserts map in the 40 kb EcoRI-a fragment were further analyzed by PstI, EcoRV, and HindIII restrictions. Five of the Tn551 insertions were found to be located on the 10.5 kb PstI fragment (PstI-alpha) known to contain the femA-femB genes (2), as analyzed by the ability of the bands of 15.7 kb to hybridize to both the Tn551 and probe pBBB31 carrying a 2.2 kb EcoRV (femA) fragment. The other six mutants, in which the Tn551-hybridizing band had a size of 17.6 kb had inserts outside of the femA-femB regions in a 12.4 kb (after subtracting 5.2 kb for the transposon) fragment, termed PstI-beta (Table 2).

These conclusions were confirmed by restriction of the same DNAs with EcoRV and hybridization with the Tn551 probe, which also allowed the assignment of the insertions to the EcoRV fragments, as indicated in Table 2. After removing the Tn551 probe, the gels were hybridized with another probe (pBBB13) carrying a 10.5 kb PstI fragment covering the entire femA-femB region, including their flanking regions (2). In the six mutants in which the insertions were located in PstI-beta, the hybridization with the pBBB13 probe generated six bands of 4.3, 4.0, 2.5, 2.2, 1.6, and 1.2 kb (FIG. 4), as was expected from previously published results (4). In the five mutants whose inserts mapped in PstI-alpha, there was a loss of one EcoRV fragment, which was replaced with another one, the molecumapped to the 1.2 kb EcoRV fragment known to contain femB (2). HindIII restriction of this mutant showed that its insertion is located in the same distal part of femB as those for a group of six previously described mutants (RUSAII-1, RUSAIII-2, RUSAIII-3, RUSA10, RUSA1H1, RUSA20F) (Table 1; reviewed in reference 9). On the other hand, mutants RUSA270 and RUSA217a, whose mutation are located in the 4.3 kb EcoRV fragment (Table 2), were shown to be distinct by HindIII restriction (Table 2). Strain RUSA217a contained two, rather than three, HindIII restriction bands, and was not analyzed further. The mutations in the last two of the PstI-alpha mutants were located in 1.6 kb and 4.0 kb EcoRV fragments, respectively, which were clearly different from the fragments in which femA (2.2 kb) or femB (1.2 kb) reside (FIG. 4). Thus, among the five new PstI-alpha mutants, at least three represent mutants with new inserts.

From the six mutants with insertions located in PstI-beta, two (RUSA101 and RUSA321) produced identical restriction fragment length polymorphisms (RFLPs), which differed from the RFLPs of the four other mutants (RUSA252, RUSA279, RUSA289, and RUSA301), each of which was unique to the strain (Table 2). Thus, the six new PstI-beta mutants represent mutants with five new insertion sites.

The second group of mutants in EcoRI includes 37 mutants located in EcoRI fragments of decreasing sizes ranging from 14.3 to 1.2 kb, which includes the fragment size (6.2 kb) of femC (Table 3).

TABLE 3

New Tn551 mutants with mutations mapping in SmaI-A but not EcoRI-a

| Strain | Ω no. | Size of restriction fragment (kb) | | | | PAP expression class | MIC ($\mu$g ml$^{-1}$) | Backcross |
|---|---|---|---|---|---|---|---|---|
| | | HindIII | EcoRI | EcoRV | PstI | | | |
| RUSA208 | COL Ω511 | 1.7 | 6.2 | 2.2 | 12.4 | 1 | 3 | RUSA208 |
| RUSA178 | COL Ω591 | 1.7 | 7.1 | 2.2 | 12.6 | 2–3 | 12–25 | |
| RUSA247 | COL Ω596 | 1.7 | 6.5 | 2.2 | 12.6 | 2 | 12 | |
| RUSA112 | COL Ω583 | 2.3 | 14 | 8.5 | 11.7 | 2–3 | 12–25 | RUSA112 |
| RUSA114 | COL Ω584 | 2.3 | 14 | 8.5 | 11.7 | 2–3 | 12–25 | RUSA114 |
| RUSA158 | COL Ω585 | 2.3 | 14 | 8.5 | 11.7 | 2 | 12 | RUSA158 |
| RUSA176 | COL Ω586 | 2.3 | 14 | 8.5 | 11.7 | 2 | 12 | RUSA176 |
| RUSA303 | COL Ω590 | 10.8 | 8.3 | 1.3 | 12.6 | 3 | 100 | |
| RUSA219 | COL Ω595 | 6.6 | 6.4 | 2.2 | 11.5 | 2–3 | 12–25 | |
| RUSA254 | | —[a] | 6.1 | 5.5 | 12.2 | 3 | 50 | |
| RUSA296 | COL Ω701 | 12.8 | 4.2 | 5.5 | 12.6 | 2–3 | 25 | |
| RUSA164 | COL Ω707 | 1.0 | 2.4 | ND[b] | 12.2 | 2 | 12 | |
| RUSA305 | COL Ω708 | 1.9 | 1.2 | 4.0 | 13.1 | 3 | 50 | |
| RUSA182 | COL Ω587 | 5.7 | 11 | 2.3 | 5.7 | 2–3 | 12–25 | |
| RUSA237 | COL Ω588 | 3.0 | 11 | 17 | 9.7 | 2 | 12 | |
| RUSA188 | COL Ω589 | 2.8 | 9.0 | 17 | 15.3 | 3 | 100 | RUSA188 |
| RUSA233 | COL Ω592 | 7.0 | 7.1 | 2.9 | 20.6 | 3 | 50 | |
| RUSA260 | COL Ω593 | 1.7 | 7.1 | 2.6 | 6.8 | 2 | 12 | |
| RUSA190 | COL Ω594 | 2.6 | 6.4 | 16 | 14.9 | 3 | 50 | |
| RUSA319 | COL Ω598 | 5.8 | 5.0 | 4.7 | 6.8 | 2–3 | 25 | |
| RUSA152 | COL Ω599 | 6.2 | 4.5 | 2.8 | 7.5 | 3 | 100 | |
| RUSA239 | COL Ω700 | 6.0 | 4.2 | 1.5 | 6.8 | 2–3 | 25 | |
| RUSA130 | COL Ω703 | 5.2 | 3.7 | 1.4 | 7.4 | 2 | 6 | |
| RUSA172 | COL Ω704 | 5.6 | 3.7 | 6.1 | 6.5 | 2–3 | 25 | |
| RUSA317 | COL Ω705 | 5.8 | 3.7 | 2.5 | 7.5 | 2 | 6 | |
| RUSA264 | COL Ω706 | 10.35 | 2.9 | 10.0 | 10.1 | 2–3 | 25 | |
| RUSA256 | | —hu c | 4.0[d] | —[c] | ND | 3 | 50 | |

[a]—, only two HindIII fragments were visible after hybridization with the Tn551 probe; the fragment containing the Tn551 right junction is missing.
[b]ND, not determined.
[c]—, two insertions.
[d]Doublet.

To summarize, the comparison of the 48 new mutants with the previously characterized femA, femB, and femC mutants that also map in SmaI-A allowed us to draw the following conclusions:

1) None of the new mutants were in the femA locus, where mutations omega 2003 and omega III-8 are located (2).

2) Only one new mutant, RUSA251 (omega 573) maps in the femB locus in the same distal part of femB as a group of six previously described mutants (RUSAII-1; RUSAIII-2; RUSAIII-3; RUSA10; RUSA1H1; RUSA20F) (for a review, see 9) (Table 1).

3) All remaining 10 new mutants that map in the SmaI-A and EcoRI-a fragments are different by HindIII restriction from the previously studied mutants in femA and femB. From these 10 mutants, 3 (omega 574–omega 576) lie in a 10.5 Kb PstI fragment (PstI-alpha) that includes femA and femB. However, they were shown by EcoRV restriction to be distinct from femA and femB (Table 2). The other 7 new mutants (omega 559 and omega 577–omega 582) in EcoRI-a lie in a distinct PstI fragment (PstI-beta). Two of these (RUSA101 and RUSA321) located in PstI-beta are identical by HindIII restriction and they were used to define a new locus referred to as femE (9). These results identify 9 new and distinct insertion sites in EcoRI-a (Table 2).

4) Eleven new mutants (omega 561–omega 571) share a common restriction pattern with EcoRI, PsI, EcoRV, and HindIII that is identical to the pattern of mutant 1H previously isolated (14) and referred to as femC (4). These eleven mutants isolated during the present work define the RUSA208 insertional cluster (17). A reexamination of previous data (17) indicates that these mutants and mutant 1H are located in PstI, EcoRI, EcoRV, and HindIII fragments of 12, 6, 2.2 and 1.7 kb, respectively.

5) The remaining 26 new mutants (omega 583–omega 599 and omega 700–omega 708) that map in SmaI-A were also studied with PstI, EcoRV, and HindIII. They could be resolved to 21 new and distinct insertion sites (Table 3).

Mutants in fragments SmaI-B, SmaI-C, SmaI-D and SmaI-E. Prior to the present work no Tn551 insertions affecting methicillin resistance were assigned to the SmaI fragments B, C, D and E. The DNAs of the four mutants located in SmaI-B, the single mutants mapped in SmaI-C and SmaI-D, and the two mutants assigned to SmaI-E were restricted with EcoRI, EcoRV, and HindIII. Each one of the mutants showed unique restriction patterns, defining 8 different insertion sites (omega 709–omega 716) (Table 4).

TABLE 4

Ne Tn551 mutants with mutations mapping in SmaI fragments B, C, D, E, and F

| Restriction enzyme and strain | Ω no. | Size of restriction fragment (kb) | | | | PAP expression class | MIC (μg ml$^{-1}$) | Backcross |
|---|---|---|---|---|---|---|---|---|
| | | HindIII | EcoRI | EcoRV | XbaI | | | |
| SmaI-B | | | | | | | | |
| RUSA281 | COL Ω709 | 5.0 | 9.6 | 1.12 | ND[a] | 1 | 3 | RUSA281 |
| RUSA262 | COL Ω710 | 5.2 | 2.1 | 16.6 | ND | 2 | 12 | RUSA261 |
| RUSA235 | COL Ω711 | 7.3 | 10.8 | 2.96 | ND | 3 | 100 | RUSA235 |
| RUSA196 | COL Ω712 | 3.0 | 10.8 | 2.96 | ND | 2–3 | 12–25 | |
| SmaI-C, RUSA223 | COL Ω713 | 5.7 | 18 | 5.1 | ND | 3 | 100 | |
| SmaI-D, RUSA162 | COL Ω714 | 2.0 | 3.4 | 4.1 | ND | 2–3 | 12–25 | |
| SmaI-E | | | | | | | | |
| RUSA206 | COL Ω715 | 3.8 | 7.1 | 1.0 | ND | 3 | 200 | |
| RUSA277 | COL Ω716 | 5.8 | 19.2 | 1.8 | ND | 2–3 | 12–25 | |
| SmaI-F | | | | | | | | |
| RUSA138 | COL Ω717 | 4.8 | ND | 18 | 4.6 | RUSA4 type | 3 | RUSA138 |
| RUSA311 | | —[b] | ND | 18 | 7.2 | RUSA4 type | 0.75 | |
| RUSA221 | COL Ω719 | 2.8 | ND | 7.1 | 8.4 | 3 | 100 | |

[a]ND, not determined.
[b]—, Only two HindIII fragments were visible after hybridization with the Tn551 probe; the fragment containing the Tn551 right junction is missing.

Mutants in fragment SmaI-F. One mutant, RUSA4 (16), was shown to have lost the ability to produce PBP2A, indicating the insertion of Tn551 in the mecA gene. The precise location of the insertion in the mecA gene was established (15). The mutation in RUSA4 lies in the SmaI-F fragment (9).

In the new Tn551, library we isolated 3 new mutants that insert in the SmaI-F fragment: RUSA138, RUSA311 and RUSA223. Whereas RUSA138 and RUSA311 have PAPs very similar to that of RUSA4 (MIC=3 μg/ml) without subpopulations of more resistant colonies, strain RUSA223 has a typical heterogeneous phenotype (class 3). By restriction analysis it was possible to confirm that the insertion sites in RUSA138 and RUSA311 (omega 717 and omega 718) lie in mecA whereas the insertion in RUSA223 (omega 719) lies outside mecA in a new auxiliary gene (Table 4).

Mutants in fragment SmaI-1. The insert in a previously isolated mutant, RUSA12F (14), was mapped in the SmaI fragment I and used to define a new locus referred to as femD (4). In the present Example, 11 new mutants were isolated and mapped in SmaI-I (omega 720–omega 730). Six of the new mutants (omega 720–omega 725) have identical restriction patterns with the enzymes EcoRI, EcoRV, PstI, and HindIII. This new cluster (RUSA315) maps in the largest HindIII fragment (HindIII-a) of 34 Kb, where RUSA12F is also located. Within this HindIII-a fragment is yet another, new mutant (RUSA266; omega 726) which may be distinguished from the RUSA315 cluster by HindIII and PstI restriction. As the sequence of RUSA12F is not available it is not known if these 7 new insertion sites and RUSA12F are in the same gene. The other four new mutants (omega 727–omega 730) have unique HindIII patterns, identifying 4 different insertion sites (Table 5).

TABLE 5

Tn551 mutants with mutations mapping in the SmaI-I fragment

| Strain | Ω no. | Size of restrictin fragment (kb) | | | | PAP expression class | MIC (μg ml$^{-1}$) | Backcross |
|---|---|---|---|---|---|---|---|---|
| | | HindIII | EcoRI | EcoRV | PstI | | | |
| RUSA12F | COL Ω558 | 34 | 10.3 | 7.5 | 5.8 | | | RUSA12F |
| RUSA315 | COL Ω720 | 34 | 10.3 | 7.5 | 5.8 | 2 | 6 | RUSA315 |
| RUSA243 | COL Ω721 | 34 | 10.3 | 7.5 | 5.8 | 2 | 6 | RUSA243 |
| RUSA184A | COL Ω722 | 34 | 10.3 | 7.5 | 5.8 | 2 | 12 | |
| RUSA299 | COL Ω723 | 34 | 10.3 | 7.5 | 5.8 | 2 | 12 | |
| RUSA313 | COL Ω724 | 34 | 10.3 | 7.5 | 5.8 | 2 | 12 | |
| RUSA18F | COL Ω725 | 34 | 10.3 | 7.5 | 5.8 | 2 | 12 | RUSA18F |
| RUSA266 | COL Ω726 | 34 | 10.3 | 7.5 | 1.8 | 2 | 6 | RUSA266 |
| RUSA168 | | —[a] | 9.8 | 0.8 | 10.8 | 2–3 | 12–25 | |
| RUSA150 | COL Ω728 | 5.6 | 9.8 | 0.8 | 10.8 | 3 | 50 | |
| RUSA122 | COL Ω729 | 1.9 | 9.8 | 1.4 | 10.8 | 3 | 50 | |
| RUSA192 | COL Ω730 | 1.25 | 4.2 | 6.5 | 12.8 | 3 | 50 | |

[a]—, only two HindIII fragments were visible after hybridization with the Tn551 probe; the fragment containing the Tn551 right junction is missing.

In summary, of the 70 new mutants with decreased methicillin resistance, the number of novel insertion sites is 58, of which only two are mecA. The 41 novel insertion sites outside mecA were distributed as follows: 27 in SmaI-A, 4 in SmaI-B, 1 i SmaI-C, I in SmaI-D, 2 in SmaI-E, 1 in SmaI-F, and 5 in SmaI-I. Only 12 of the insertions seem identical to previously described Tn551 sites: the single new femB mutant RUSA251 and the eleven mutants that appear to belong to the femC group.

Transduction crosses an analysis of transductants. A number of the auxiliary mutations isolated were transduced back into the parental strain COL. All backcrosses analyzed both by PAP analysis and by HindIII restriction analysis, as described in Materials and Methods, are listed in Tales 2 to 5. In all of these 21 crosses, 100% cotransduction of the $ery^R$ marker with reduced methicillin resistance was obtained. There was no evidence of reversion to resistance or transposition.

Figure 5:
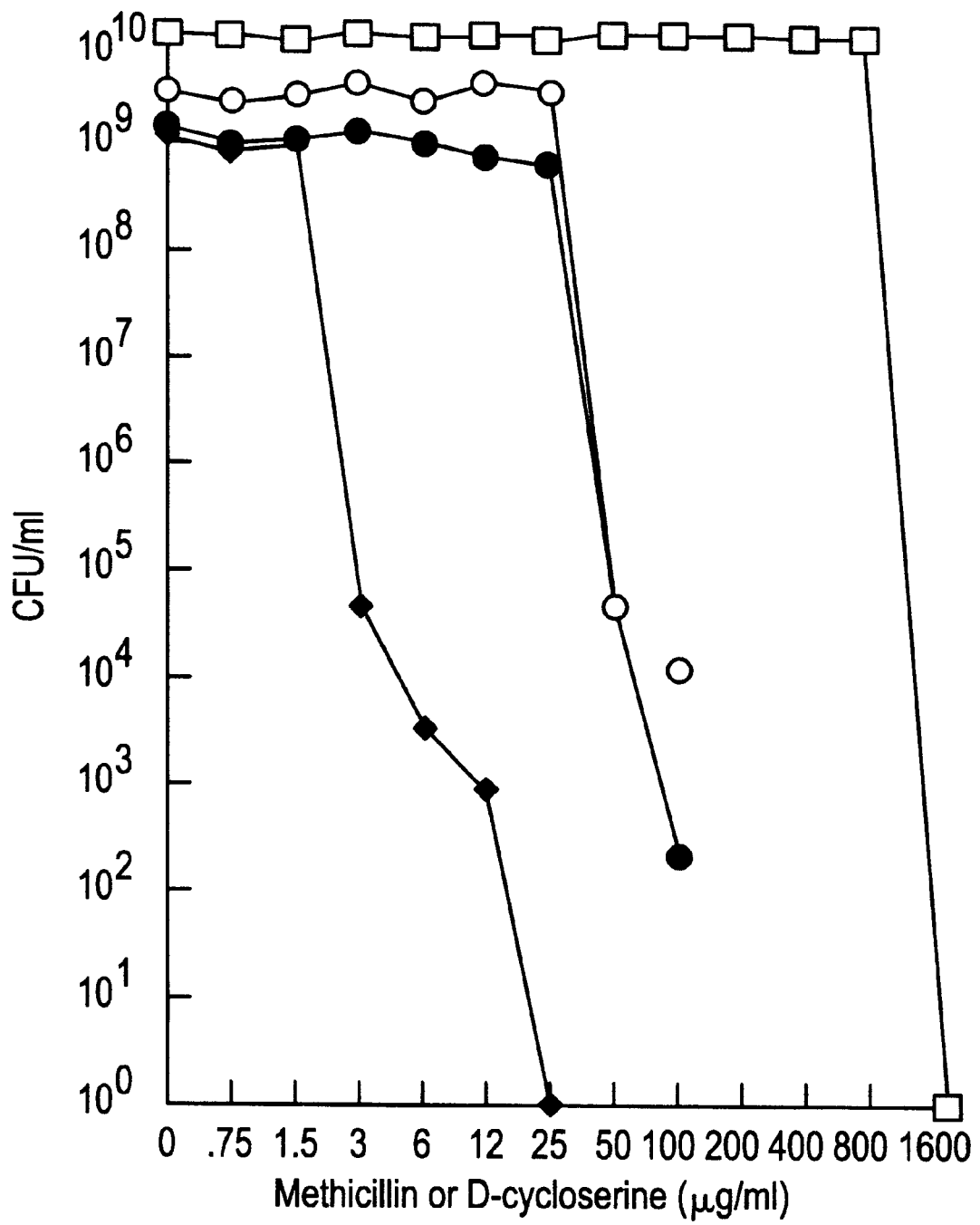
FIG. 5. Effect of a Tn551 mutation on the phenotypic expression of methicillin resistance and resistance to D-cycloserine. The antibiotic resistance phenotypes of the parental MRSA strain COL (□) and its Tn551 mutant RUSA10 (♦) were determined by population analysis, as described in the Methods for Example 1, infra. The same method was also used to compare the effect of RUSA10 mutation on the expression of resistance against another antibiotic, D-cycloserine, in strain COL (○) and the mutant RUSA10 (●).

Effects of the Tn551 mutation on bacterial physiology. Several of the auxiliary mutants that were analyzed showed reduced growth rates, as compared to the parental bacterium. This was also true when the Tn551 mutation was crossed out of the MRSA genetic background into a laboratory-derived methicillin resistant step mutant, strain M100 (Tonin and Tomasz, 1986, Antimicrob. Agents Chemother. 35:124–129). As to the effect of the Tn551 insertion on the phenotypic expression of antibiotic resistance traits other than resistance against beta lactams, this was tested with mutant RUSA10 using susceptibilities to D-cycloserine, tetracycline, ofloxacin, and gentamycin. In contrast to the massive reduction in methicillin resistance level and the appearance of heterogeneous phenotype, the RUSA10 mutation did not change the antibiotic susceptibilities (MIC values) of the parental strain COL to tetracycline (200 µg/ml), ofloxacin (1.5 µg/ml), gentamycin (0.75 µg/ml), or D-cycloserine (50 µg/ml) and the expression of resistance to these antibiotics remained homogeneous (FIG. 5).

Discussion

The new transposon library described here has produced evidence for a surprisingly large number of chromosomal sites that can profoundly influence the level of methicillin resistance. Only two of the new Tn551 inserts were in the mecA gene. The rest of the insertion sites distributed widely in 7 out of the 16 chromosomal SmaI fragments. The largest number of mutations—48—was in fragment A and the rest in fragments B (4), C (1), D (1), E (2), and I (12). Thus, it appears that the overwhelming majority of the new Tn551 mutants are in auxiliary (22) or fem (3) genes, i.e., genetic determinants needed for the phenotypic expression of optimal (high) levels of methicillin resistance. Previous work has described 12 Tn551 MRSA mutants with reduced resistance. The first one of these, omega 2003, has led to the identification of the femA gene by Berger-Bachi (1,2). A second mutant, III/8 (14), was also mapped in femA (2). Six additional mutants were mapped in the distal part of a second locus femB (2,9) and, more recently, a mutant was also identified in the ORF of femB (13). Mutants 1H and 12F (14) have led to the identification of genes femC and femD, respectively (4). A single Tn551 mutant, RUSA4 (16), was located inside the mecA gene (15) in the SmaI chromosome fragment F (9).

In contrast to these 12 previously described insertional mutants (defining the fem genes A, B, C and D) which were located either on SmaI fragment A or I, the large crop of new insertion sites described in this Example were scattered over seven of the sixteen SmaI fragments, fragments A, B, C, D, E, F and I. The finer physical mapping by the restriction nucleases EcoRI, PstI, EcoRV, and HindIII allows one to identify 58 distinct, as yet undescribed Tn551 insertion sites, each one of which results in reduction of methicillin resistance. Only two sites, mapped in the mecA gene, resulted in a homogeneous reduction of resistance. The rest of the Tn551 mutants exhibited heterogeneous phenotypes in which the resistance level of the majority of cells was reduced (from the extremely high MIC of the parental cells—1600 µg/ml) to a range of MICs from 1.5 up to 200 µg/ml.

Each of these heterogeneous phenotypes were stable and characteristic of the particular mutant and in genetic backcrosses these unique phenotypes were reproduced with remarkable fidelity.

It is not clear how many new genetic determinants are defined by the new inserts. Nevertheless, the large physical distance between the four insertion sites located in the SmaI fragment B, the single insertion sites in fragments C and D, and the two distant sites on fragments E and F are likely to represent at least nine new genetic determinants. This number does not include the several new genes defined by the new Tn551 mutants located on SmaI fragments A and I.

The genes implicated in the transposon mutagenesis may be involved with the structure of staphylococcal cell wall since previous studies have shown that the femA and B mutants had abnormal peptidoglycan crossbridge structures (5,6,7) and a femC mutant was shown to be blocked in the amidation of the alpha-carboxyl group of the D-glutamic acid residues in the muropeptide subunits (17). A model for the mechanism of how abnormalities of muropeptide structure may lead to reduction in beta lactam antibiotic resistance level has been proposed recently (9).

The consistent appearance of heterogeneity among virtually all auxiliary mutants described so far is not well understood. It is possible that in most of these mutants the Tn551 insert is either in the promoter or in the distal part of the open reading frame, allowing partial read-through of the gene. This is consistent with the finding that normal (parental) muropeptide species is present (albeit in greatly reduced quantities) in the cell walls of several of the auxiliary mutants analyzed so far. It is possible indeed that insertion in the ORFs of these genes is lethal. The reduction in growth rate of the femB mutant RUSA10, in the absence of antibiotic is consistent with this suggestion. The auxiliary mutants may indeed represent "methicillin-conditional" mutants in essential genes of staphylococcal peptidoglycan metabolism.

EXAMPLE 2

Reduced Methicillin Resistance in a New *Staphylococcus aureus* Transposon Mutant that Incorporates Muramyldipeptides into the Cell Wall Peptidoglycan Screening of a new Tn551 library constructed in the background of a highly methicillin-resistant *Staphylococcus aureus* strain identified a new insertion site located on the SmaI B-fragment of the chromosome which reduced the minimal inhibitory concentration value of the parent (1600 µg/ml) to 25–50 µg/ml in the mutant, caused heterogeneous expression of resistance, and abnormality of peptidoglycan composition: the unsubstituted pentapeptide was absent and alanyl-glutamate and alanyl-isoglutamate- containing muropeptides were incorporated in the cell wall. There was an accumulation of large amounts of the UDP-linked muramyl-dipeptide in the cytoplasmic wall precursor pool of the mutant. Both reduced (heterogeneous) antibiotic resistance and all the biochemical abnormalities were reproduced in genetic backcrosses using transduction with phage 80 alpha. Mutant RUSA 235 appears to be impaired in the biosynthesis of the staphylococcal cell wall precursor muropeptide before the lysine addition step. We propose to provisionally call the gene inactivated in this mutant femF.

Materials and Methods

Bacterial strains and growth conditions. The highly and homogeneously methicillin resistant parental strain COL and Tn551 mutants used in this study are listed in Table 1, supra. Growth medium and methods used for the cultivation of the strains were described earlier (18). Population analysis profiles were done as described (8).

Selection of RUSA235 by Tn551 transposition and genetic crosses. Tn551 transposition (19) and transduction with phage 80 alpha (18) were carried out by previously described methods. The transduction crosses were performed using the newly isolated mutant RUSA235 as donor and the homogeneously resistant parental strain COL as recipient. Among the 46 transductants analyzed the cotransfer of the Tn551 marker (erythromycin) and reduced methicillin resistance was 100%.

Preparation of chromosomal DNA for conventional and pulsed-field gel electrophoresis (PFGE). Preparation of chromosomal DNA from strain COL and the various Tn551 insertional mutants was carried out as previously described (10).

Preparation of DNA probes and hybridization. The whole plasmid pRT1 (that contains a 4 Kb HpaI-XbaI internal fragment from transposon Tn551) was used as probe (15). Standard methodology was followed for $^{32}$P-labeling of the probes by nick translation, prehybridization and hybridization (20). A nonradioactive labeling system (ECL) from Amersham (Arlington Heights, Ill.) was used according to the manufacturer's instructions. For blotting of conventional gels to nitrocellulose membranes (Schleicher & Schuell BA85, USA) a vacuum blotting apparatus was used (Vaccublot, Pharmacia/LKB) according to the manufacturer's instructions. For the blotting of pulsed-field gel electrophoresis gels we followed a previously described method (10).

Restriction digestion. Restriction digestions with SmaI, EcoRI, EcoRV, PstI, and HindIII nucleases were carried out according to the manufacturers' recommendations (New England Biolabs, Inc.).

Conventional and pulsed-field gel electrophoresis. These were carried out as described in Example 1, supra (see reference 10).

Preparation of the muropeptides and separation with reversed-phase high performance liquid chromatography (HPLC). Muropeptides were prepared from cell walls as previously described (5) except that the alkaline phosphatase step was omitted. The structure of the muropeptides was determined by amino acid and mass spectrometric analysis (17).

N-acetyl-D-glucosaminyl-(beta-4)-N-acetylmuramyl-L-alanyl-D-isoglutamine-(GM DP) was obtained from Calbiochem (San Diego, Calif.). The GMDP analog with free glutamic acid residue was kindly provided by the C—C Biotech Corporation, Poway, Calif.

Preparation of the UDP-linked precursor and analysis with HPLC. Cytoplasmic pools of UDP-linked peptidoglycan precursor were extracted by a modification of a previously described method (Handwerger et al., 1994, J. Bacteriol 176:260– 264). Cells were grown to mid-logarithmic phase in TSB at 37° C. with aeration, chilled and harvested by centrifugation, washed in 0.9% saline and extracted with cold trichloroacetic acid (final concentration of 5%) for 30 min, at 4° C. The extract containing the pool of precursors was separated by gel filtration on a Sephadex G-25 column (Pharmacia, Alameda, Calif.) eluted with water. Hexosamine-containing fractions identified by the assay of Ghuysen et al. (1966, Methods Enzymol. 8:684–699) were combined and lyophilized. Separation of the muropeptides by HPLC was performed essentially by the method of Flouret et al. (1991, Anal. Biochem. 114:59–63) with some modifications. Samples were applied to a 3.9×300 mm reverse-phase column (uBondapack C18, Waters Chromatography Division, Millipore Co., Milford, Mass.) guarded by a 15×3.2 mm Perisorb RP-18 precolumn (Pierce Chemical Co., Rockford, Ill.). The column was operated under isocratic elution at room temperature with 0.05 M ammonium phosphate, pH 5. 1, at a flow rate of 0.5 ml/min, which was changed to 2.0 ml/min at 25 min. Eluted compounds were detected by absorption at 254 nm (Spectroflow 757, Kratos Analytical Instruments, Ramsey, N.J.), the areas of the peaks of interest were added together, and individual peaks were expressed as a percentage of this total. Peaks representing cell wall precursors prepared from S. aureus 209P grown in TSB in the presence of cycloserine (120 μg/ml) and vancomycin (4 μg/ml) were used as reference for determination of retention times of the tripeptide and pentapeptide precursor compounds. The major uridine-diphosphate (UDP) containing peak from the cytoplasmic precursor extract of RUSA235 was collected, desalted and analyzed for amino acid composition. UDP-N-acetylglucosa- mine from Sigma (St. Louis, Mo.) was used as a standard. Boiling samples for 3 min in 0.1 M HCl before loading onto the column was used to identify UDP-containing peaks.

Results

Figure 6:
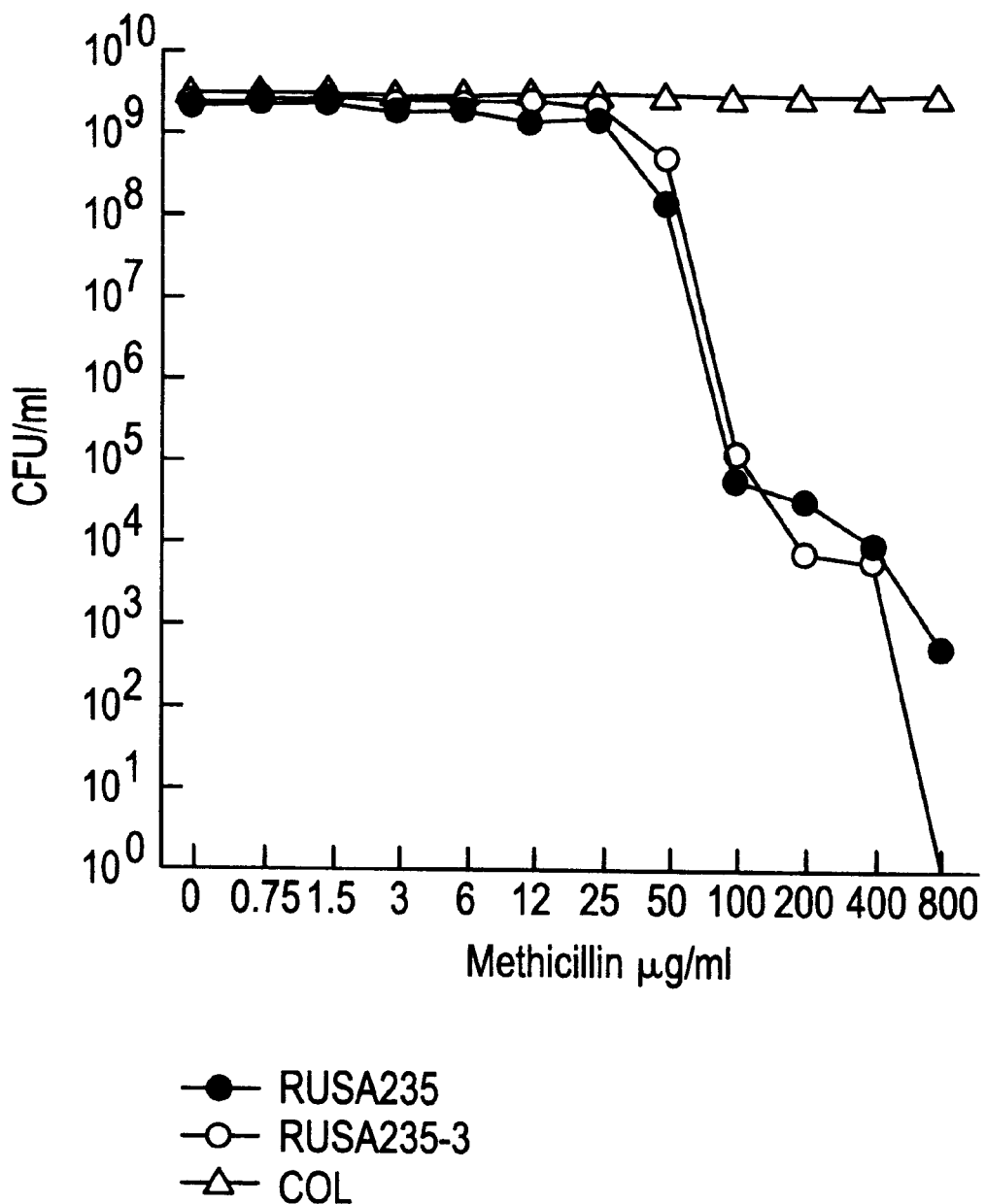
FIG. 6. Phenotypic expression of methicillin resistance of mutant RUSA235 and its backcross RUSA235-3. Bacterial cultures were grown in tryptic soy broth with aeration to stationary phase. The bacteria were plated on agar containing various concentrations of methicillin as described for the method of population analysis (8). CFU, colony-forming units; (●), RUSA235; (○), RUSA235-3; (Δ), COL.

Reduced methicillin resistance in mutant RUSA235. FIG. 6 shows the population analysis profiles of the mutant RUSA235 (omega 711) and one of its backcrosses (transductant into COL) RUSA235-3. The Tn551 insertion caused a change in the resistance phenotype from homogeneous (parental) to a heterogeneous one and a reduction of the MIC from 1600 μg/ml to 25–50 μg/ml for the majority of the mutant cells.

Physical location of the Tn551 insert. Chromosomal DNA prepared from mutant RUSA235 was restricted with the endonuclease SmaI. DNA fragments separated by PFGE were hybridized with a Tn551 DNA probe to locate the insert. The transposon in strain RUSA235 was located in the SmaI-B fragment.

Figure 7:
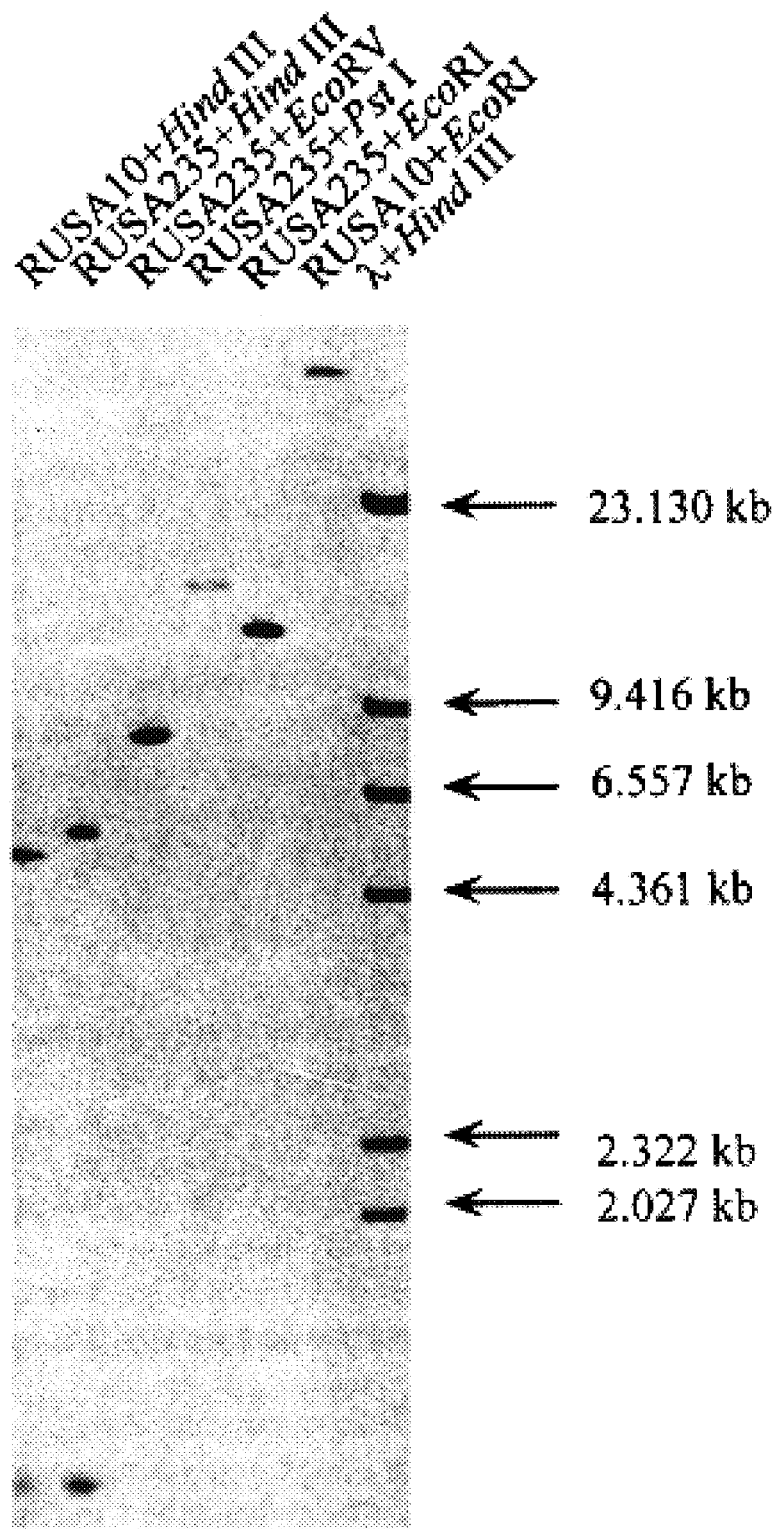
FIG. 7. Restriction, fragmentation pattern of mutant RUSA235. Chromosomal DNA isolated from RUSA235 was restricted with different restriction enzymes, and the fragments were separated by pulsed-field gel electrophoresis in a Chef-DRII apparatus (Bio-Rad) for 15 h at 14° C. The Tn551 inserts were located after Southern hybridization and probing with a nonradioactive Tn551 probe. The second through fifth lanes contain RUSA235 DNA restricted with HindIII, EcoRV, PstI, and EcoRI, respectively. The first and sixth lanes include as controls HindIII and EcoRI digests of a femB mutant (RUSA10). The seventh lane contains λ-DNA restricted with HindIII as a molecular size marker.
Figure 8:
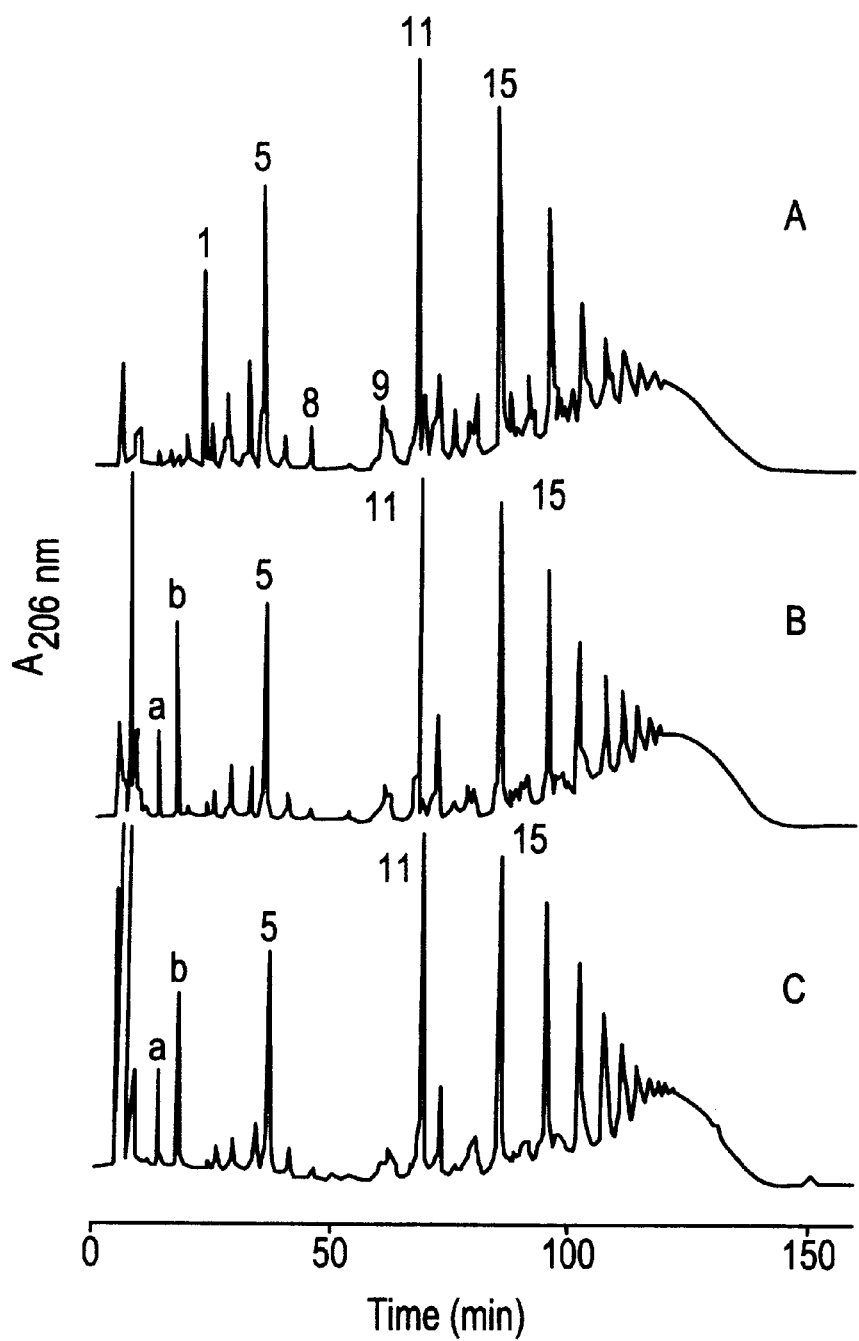
FIG. 8. HPLC elution profiles of muropeptides isolated from the parental strain, mutant RUSA235, and its backcross. Peptidoglycan was isolated and hydrolyzed with muramidase, and the resulting muropeptides were separated by HPLC as described under "Experimental Procedures." A: muropeptide pattern of COL; B: muropeptide profile of RUSA235; C: muropeptide profile of RUSA235-3. For the structures of muropeptides 1,5,8,9,11, and 15, refer to Reference 5.

Additional restriction digests were prepared using four other endonucleases (HindIII, EcoRV, EcoRI, PstI) in order to more accurately characterize the insertion site in mutant RUSA235 (FIG. 7). This analysis showed that the insertion site in RUSA235 could be located in restriction fragments of the following sizes: HindIII (7.3 Kb), EcoRV (3 Kb), EcoRI (10.8 Kb); PstI (12 Kb).

The identity of the insertion site in mutant RUSA235 and several of its backcrosses into COL (transductants RUSA235-3, -9, -14) was established by HindIII restriction of their DNAs followed by hybridization with the Tn551 probe (data not shown).

Muropeptide composition of the peptidoglycan of RUSA235 as determined by HPLC and chemical analysis. The HPLC elution profiles for the parental strain COL, RUSA235 and its backcross RUSA235-3, are shown in FIG.

8. Except for peak 1, each major parental muropeptide species was present in the HPLC profile of mutant 235, and peaks 8 and 9 were only present in reduced quantities. A novel feature of the HPLC profile of mutant RUSA235 was the appearance of new peaks at retention times of 13.6 (peak a) and 17.6 (peak b) min.

These new peaks were collected and analyzed for amino acid composition and molecular size (mass spectrometry).

TABLE 7

UDP-linked peptidoglycan of mutant RUSA235 and its parental strain (COL)
The relative amounts of the compounds (peaks I–VI) are expressed as percentages (calculated from the UV absorbance of peaks in HPLC elution profiles). Data represent the means of three experiments. UDP-GlcNAc, uridine diphospho-N-acetylglucosamine; UDP-MurNAc, uridine diphospho-N-acetylmuramic acid, Ala, L-alanine; Glu, D-glutamate; Lys, L-lysine; Penta, L-alanine: D-glutamate: L-lysine: D-alanine: D-alanine.

| Strain | I UDP-GlcNAc % | II UDP-MurNAc % | III UDP-Mur-Ala % | IV UDP-Mur-Ala-Glu % | V UDP-Mur-Ala-Glu-Lys % | VI UDP-Mur-Penta % | Total hexosamines nmol |
|---|---|---|---|---|---|---|---|
| COL | 20 ± 2 | 28 ± 3 | 41 ± 3 | 0 | 0 | 11 ± 2 | 42 ± 8 |
| RUSA235 | 0 | 10 ± 3 | 22 ± 4 | 63 ± 5 | 0 | 3 ± 1 | 252 ± 30 |

Figure 9:
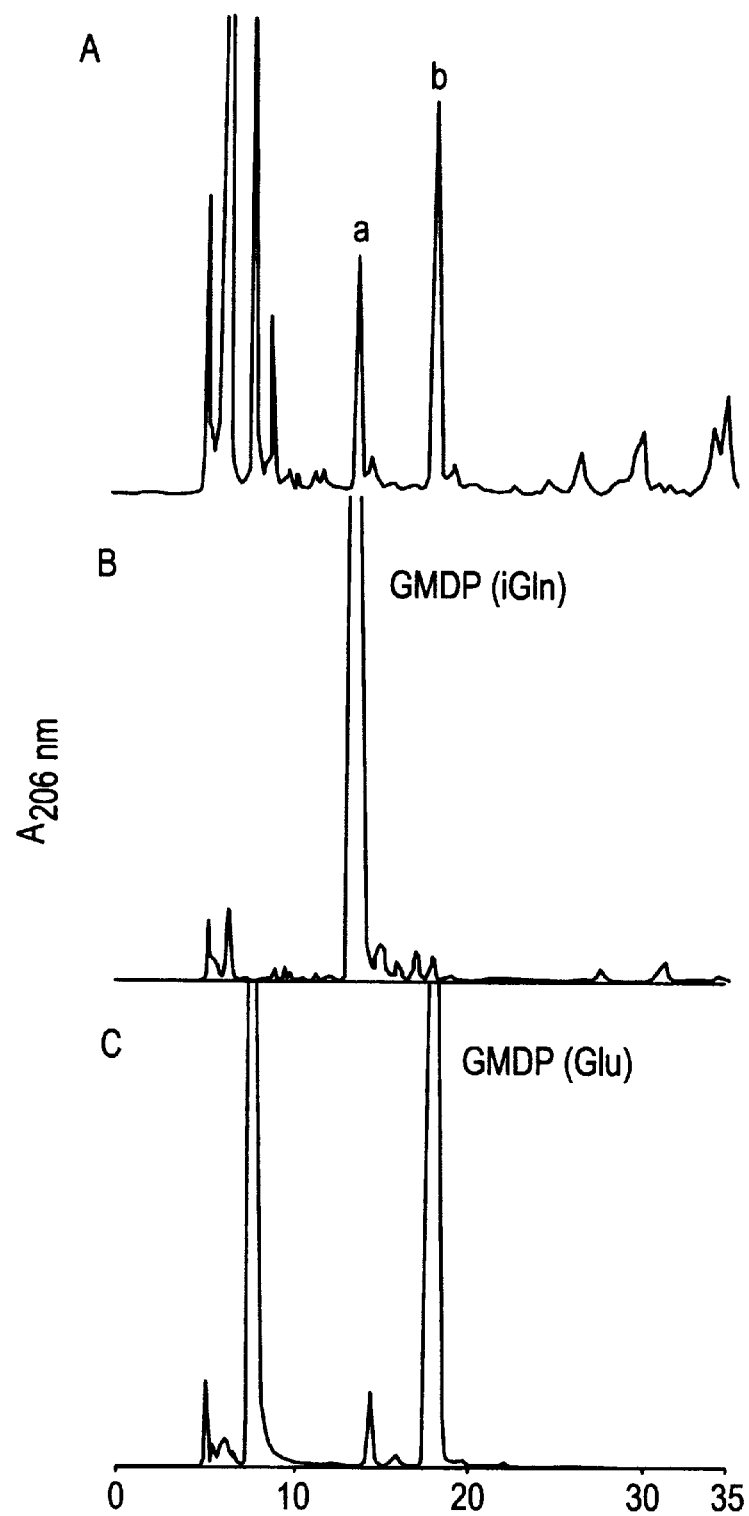
FIG. 9. Section of the HPLC profile of mutant RUSA235 showing the two newly identified peaks and comparison with the two disaccharide dipeptide standards. The elution profile and retention time of peak from RUSA235 (A) are identical to those of the GMDP standard with isoglutamine (iGln; B). Peak b from RUSA235 has an elution profile identical to that of the GMDP standard with glutamic acid (C).

Table 6 shows the retention times, amino acid composition and molecular size for the two new muropeptide species. Both compounds were identified as disaccharide dipeptides with identical amino acid composition (1 mole each of alanine and glutamic acid), but the two muropeptides differed from one another by 1 mass unit. The peak with shorter retention time coelutes with a commercially available muropeptide standard containing isoglutamine. The peak with the longer retention time coeluted with the GMPD standard containing glutamic acid residue (FIG. 9). This is in accordance with previously published results (17), which showed that in the HPLC system employed here, muropeptides in which the isoglutamine (iGln) was replaced by a free glutamate eluted with longer retention times.

TABLE 6

Amino acid analysis and molecular masses of the anomalous muropeptides isolated from the muramidase digest of the peptidoglycan of mutant RUSA235

| Muropeptide[a] | HPLC retention time min | Amino acid analysis Glx | Ala | Lys | Gly | Mass spectrometry $(M + H)^{+c}$ |
|---|---|---|---|---|---|---|
| a | 13.6 | 1 | 1.25 | ND[b] | ND | 698.3 |
| b | 17.6 | 1 | 1.08 | ND[b] | ND | 699.3 |

[a]See Figure
[b]ND, not detected
[c]$(M + H)^+$ ion of the reduced muropeptide

UDP-lined cell wall precursor pool of parental strain COL and mutant RUSA235.

Figure 10:
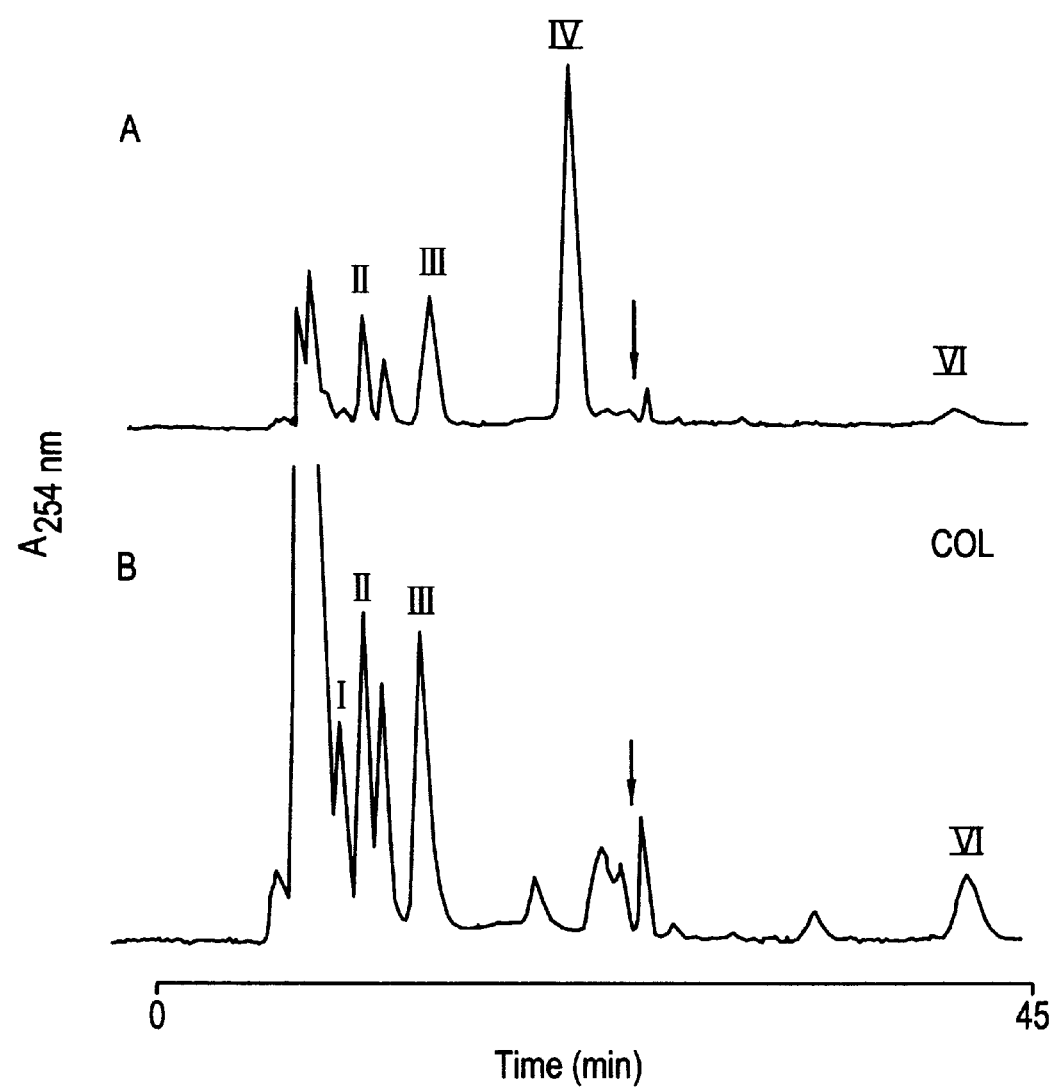
FIG. 10. Separation of cytoplasmic peptidoglycan precursors isolated from the parental strain and mutant RUSA235 by HPLC. Cytoplasmic precursors were isolated and separated by HPLC as described under "Experimental Procedures." The flow rate was changed from 0.5 to 2.0 ml/min at the times indicated (↓). A: elution profile of mutant RUSA235; B: elution pattern of the parental strain (COL). Peak numbers correspond to compounds in Table 7.

FIG. 10 shows the HPLC elution profiles of UDP-linked precursors extracted from the parental and mutant staphylococci. Table 7 shows that quantitative differences between the composition of parental and mutant cell wall precursor pool. Peak IV, a component absent from the precursor pool of parental cells, has accounted for over 60% of the UDP-linked muropeptides in the mutant extract. This material was isolated and identified as UDP-N-acetyl-muramyl-alanyl-glutamate on the basis of chemical analysis (UV spectra, Elson-Morgan reaction and quantitative amino acid analysis).

Discusssion

The screening of a library of Tn551 mutants of MRSA for reduced methicillin resistance has already identified several transposon mutants with altered peptidoglycan composition, either in the stem peptides or in the crossbridges. Previously described mutants located outside the mecA gene had transposon inserts in the SmaI A fragment (mutants omega 2003, RUSA10, RUSA208—with inserts in the auxiliary genes femA, femB, and femC) or in the SmaI I fragment (RUSA12F—femD) of the staphylococcal chromosome (4, 9, 11, 17). Mutant RUSA235 differs from these previous transposon mutants in that the insertion is located in the SmaI B fragment. We propose to refer to the inactivated auxiliary gene as femF, following the currently used, provisional nomenclature.

The peptidoglycan of RUSA235 is composed of the same muropeptide species as the parental strain in the same proportions and same degree of crosslinking (as judged by the comparable amounts o cross-linked peptides 9 and higher), except for the reduced amounts of the unsubstituted disaccharide pentapeptide monomer (and muropeptides 8 and 9) and the presence of the two novel disaccharide dipeptides. Each of these two new muropeptides contained one mole each of alanine and glutamate, but lacked lysine, glycine, and any other amino acids. The two muropeptides differed from one another by one mass unit. These data and the retention times of the components during reverse phase HPLC indicate that they are composed of disaccharide dipeptides in which the first amino acid is alanine and the amino acid at the second position is either isoglutamine or glutamic acid. Analysis of the cytoplasmic peptidoglycan precursor pool of RUSA235 revealed an accumulation of the UDP-linked muramyl-dipeptide containing equimolar amounts of alanine and glutamic acid and reduced level of the UDP-linked muramyl-pentapeptide. These data indicate that the RUSA235 mutation is in a gene (femF) responsible for the biosynthetic step in which the L-lysine residue is added to the UPD-linked muramyl dipeptide chain. A quantitative impairment of the muropeptide synthetic route at this step may explain the observed deficit in muropeptide species which contain unsubstituted pentapeptide units in the mutant peptidoglycan.

Some of the properties of RUSA235 are reminiscent of a S. aureus conditional mutant TOF-95 (Good and Tipper, 1972, J. Bacteriol 111:231–241) and RUS 1 (Chatterjee and Young, 1972, J. Bacteriol 111:220–230), both of which are defective in cell wall precursor synthesis which also showed accumulation of UDP-linked muramyl dipeptide cell wall precursors and a defective lysine adding enzyme. However, in contrast to TOF-95, RUSA235 was capable of growth at elevated temperature (43° C.) without osmotic supplementation of the medium.

The reasons for the drastic reduction in the methicillin MIC value in mutant RUSA235 are not clear. In a previous report (9), we suggested that the high methicillin MIC values of some MRSA strains may be related to the effective competition by the normal muropeptide precursors for a critical site on the PBP2A protein (i.e., the mecA product). In this model, wall precursors of abnormal chemical structure would be less effective competitors, thus allowing acylation of the active site of the cell wall synthetic enzyme (presumably PBP2A) to occur at a lower concentration of the antibiotic (9). Other alternative mechanisms cannot be excluded. The normal muropeptide precursors in which mutant RUSA235 shows a deficit may perform some as yet undefined signaling role in wall synthesis. The muramyl dipeptide residues lacking the diaminoacid component (and thus unable to participate in crosslinking) may incorporate into some structurally critical positions in the peptidoglycan and this may, indirectly, jeopardize the integrity of wall structure during perturbation of wall synthesis by antibiotics.

References

1. Berger-Bachi, B. 1983. Insertional inactivation of staphylococcal methicillin resistance by Tn551. J. Bacteriol. 154:479–487.
2. Berger-Bachi, B., L. Barberis-Maino, A. Strassle, and F. H. Kayser. 1989. femA, a host-mediated factor essential for methicillin resistance in *Staphylococcus aureus*: molecular cloning and characterization. Mol. Gen. Genet. 219:263–269.
3. Berger-Bachi, B., A. Strassle, L. Barberis-Maino, W. Tesch, C. Ryffel, and F. H. Kayser. 1990. femA, a host-mediated trans-acting factor essential for methicillin resistance in *Staphylococcus aureus*. In Molecular Biology of the Staphylococci. (R. P. Novick, ed.). pp. 509–520, VCH Publishers, Inc., New York.
4. Berger-Bachi, B., A. Strassle, J. E. Gustafson, and F. H. Kayser. 1992. Mapping and characterization of multiple chromosomal factors involved in methicillin resistance in Staphylococcus aureus. Antimicrob. Agents Chemother. 36:1367–1373.
5. De Jonge, B. L. M., Y. -S. Chang, D. Gage, and A. Tomasz. 1992. Peptidoglycan composition of a highly methicillin-resistant *Staphylococcus aureus* strain: the role of penicillin binding protein 2A. J. Biol. Chem. 267:11248–11254.
6. De Jonge, B. L. M., Y. -S. Chang, D. Gage, and A. Tomasz. 1992. Peptidoglycan composition in heterogeneous Tn551 mutants of a methicillin resistant *Staphylococcus aureus* strain. J. Biol. Chem. 267:11255–11259.
7. De Jonge, B. L. M., T. Sidow, Y. -S. Chang, H. Labischinski, B. Berger-Bachi, D. A. Gage, and A. Tomasz. 1993. Altered muropeptide composition in *Staphylococcus aureus* strains with an inactivated femA locus. J. Bacteriol. 175:2779–2782.
8. De Lencastre, H., A. Figueiredo, K. Urban, J. Rahal, and A. Tomasz. 1991. Multiple mechanisms of methicillin resistance and improved methods for detection in clinical isolates of *Staphylococcus aureus*. Antimicrob. Agents Chemother. 35:632–639.
9. De Lencastre, H, B. L. M. de Jonge, P. R. Matthews, and A. Tomasz. 1994. Molecular aspects of methicillin resistance in *Staphylococcus aureus*. J. Antimicrob. Chemother. 33:7–24.
10. De Lencastre, H., I. Couto, I. Santos, J. Melo-Cristino, A. Torres-Pereira, and A. Tomasz. 1994. Methicillin-resistant *Staphylococcus aureus* disease in a Portuguese hospital: characterization of clonal types by a combination of DNA typing methods. Eur. J. Clin. Microbiol. Infect. Dis. 13:64–73.
11. Gustafson, J., A. Strassle, H. Hachler, F. H. Kayser, and B. Berger-Bachi. 1994. The femC locus of *Staphylococcus aureus* required for methicillin resistance includes the glutamine synthetase operon. J. Bacteriol. 176:1460–1467.
12. Hartman, B. J., and A. Tomasz. 1986. Expression of methicillin resistance in heterogeneous strains of *Staphylococcus aureus*. Antimicrob. Agents Chemother. 29:85–92.
13. Henze, U., T. Sidow, J. Wecke, H. Labischinski, and B. Berger-Bachi. 1993. Influence of femB on methicillin resistance and peptidoglycan metabolism in *Staphylococcus aureus*. J. Bacteriol. 175:1612–1620.
14. Kornblum, J., B. J. Hartman, R. P. Novick, and A. Tomasz. 1986. Conversion of a homogeneously methicillin resistant strain of *Staphylococcus aureus* to heterogeneous resistance, by Tn551-mediated insertional inactivation. Eur. J. Clin. Microbiol. 5:714–718.
15. Matthews, P., and A. Tomasz. 1990. Insertional inactivation of the mec gene in a transposon mutant of a methicillin-resistant clinical isolate of Staphylococcus aureus. Antimicrob. Agents Chemother. 34:1777–1779.
16. Murakami, K., and A. Tomasz. 1989. Involvement of multiple genetic determinants in high-level methicillin-resistance in Staphylococcus aureus. J. Bacteriol. 171:874–879.
17. Ornelas-Soares, A., H. de Lencastre, B. de Jonge, D. Gage, Y. -S. Chang, and A. Tomasz. 1993. The peptidoglycan composition of a *Staphylococcus aureus* mutant selected for reduced methicillin resistance. J. Biol. Chem. 268:26268–26272.
18. Oshida, T., and A. Tomasz. 1992. Isolation and characterization of a Tn551-autolysis mutant of Staphylococcus aureus. J. Bacteriol. 174:4952–4959.
19. Pattee, P. A. 1981. Distribution of Tn551 insertion sites responsible for auxotrophy on the *Staphylococcus aureus* chromosome. J. Bacteriol. 145:479–488.
20. Sambrook, J., E. F. Fritsch, and T. Maniatis T (eds.). 1989. Molecular Cloning, A Laboratory Manual, 2nd edition. Cold Spring Harbor Laboratory Press, Cold Spring Harbor, N.Y.
21. Shaw, J. H., and D. B. Clewell. 1985. Complete nucleotide sequence of macrolide-lincosamine- streptogramin B-resistance transposon Tn917 in *Streptococcus faecalis*. J. Bacteriol. 164:782–796.
22. Tomasz, A. 1990. Auxiliary genes assisting in the expression of methicillin resistance in Staphylococcus aureus. In: Molecular Biology of the Staphylococci (R. P. Novick, ed.). pp. 565–583, VCH Publishers, Inc., New York.

These data indicate that interference with the peptidoglycan biosynthesis at the cytoplasmic level affects methicillin resistance in *S. aureus*.

This invention may be embodied in other forms or carried out in other ways without departing from the spirit or essential characteristics thereof. The present disclosure is therefore to be considered as in all respects illustrative and not restrictive, the scope of the invention being indicated by the appended Claims, and all changes which come within the meaning and range of equivalency are intended to be embraced therein.

It is also to be understood that all base pair sizes given for nucleotides and all molecular weight information for proteins are approximate and are used for the purpose of description.

Various references are cited throughout this specification, each of which is incorporated herein by reference in its entirety.

What is claimed is:

1. A purified antibiotic-resistant *Staphylococcus aureus* strain having a mutation in a gene comprising a DNA sequence as set forth in SEQ ID NO:1, wherein said strain is characterized by:
   a. increased sensitivity to an antibiotic to which a parent of said strain is resistant; and
   b. said mutation is located in the SmaI-I fragment of the chromosome of said strain.

2. The strain of claim 1 in which the antibiotic is a beta lactam antibiotic.

3. The strain of claim 2 in which the antibiotic is methicillin.

4. The strain of claim 1 in which the mutation in said gene is caused by insertion of transposon Tn551 into said gene.

5. An isolated nucleic acid segment which encodes a protein associated with antibiotic resistance in a *S. aureus* bacterium, wherein said nucleic acid is located on the SmaI-I fragment of the chromosome of *S. aureus*, said nucleic acid segment selected from the group consisting of:
   (a) the nucleotide sequence consisting of SEQ ID NO: 1; and
   (b) a nucleotide sequence consisting of a degenerate variant which encodes the protein encoded by the nucleotide sequence of (a).

6. A recombinant vector comprising the nucleic acid of claim 5 operatively associated with a heterologous expression control sequence.

7. A bacterial cell comprising the recombinant vector of claim 6.

* * * * *

SEQUENCE LISTING (1) GENERAL INFORMATION:

(iii) NUMBER OF SEQUENCES: 1

(2) INFORMATION FOR SEQ ID NO:1:

(i) SEQUENCE CHARACTERISTICS:
        (A) LENGTH: 2739 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (vi) ORIGINAL SOURCE:
        (A) ORGANISM: Staphylococcus aureus
        (B) STRAIN: RUSA 168

(xi) SEQUENCE DESCRIPTION: SEQ ID NO:1:

```
AAGATAAATA TTTTTAATAA GTAGGAGTGT AATGAAATGA ATCTTAATAT AGAAACAACC      60

ACTCAAGATA AATTTTACGA AGTTAAAGTC GGTGGAGAAT TAGATGTTTA TACTGTGCCT     120

GAATTAGAAG AGGTTTTAAC ACCTATGAGA CAAGATGGAA CTCGTGATAT TTATGTTAAT     180

TTAGCAAATG TGAGTTATAT GGATTCGACA GGTTTAGGTT TATTCGTAGG TACATTAAAA     240

GCATTAAACC AAAATGATAA AGAACTATAC ATTTTAGGTG TGTCAGATCG TATCGGTAGA     300

CTATTTGAAA TTACTGGTCT TAAGGATTTA ATGCATGTTA ATGAAGGAAC GGAGGTCGAA     360

TAACATGCAA TCTAAAGAAG ATTTTATCGA AATGCGCGTG CCAGCATCGG CAGAGTATGT     420

AAGTTTAATT CGTTTAACAC TTTCTGGCGT TTTTTCGAGA GCTGGTGCTA CATATGATGA     480

TATTGAAGAT GCCAAGATTG CAGTTAGTGA AGCTGTGACA AATGCAGTTA ACATGCATA      540

CAAAGAAAAT AACAATGTGG GCATTATTAA CATATATTTT GAAATTTTAG AAGATAAAAT     600

TAAAATTGTT ATTTCTGATA AAGGTGACAG TTTTGATTAT GAAACAACTA AATCAAAAAT     660

AGGTCCTTAC GATAAAGACG AAAATATAGA CTTTTTACGC GAAGGTGGCC TAGGTTTATT     720

TTTAATCGAA TCTTTAATGG ATGAAGTCAC AGTATATAAA GAATCTGGTG TGACAATCAG     780

TATGACTAAG TATATAAAAA AAGAGCAGGT GCGAAATAAT GGCGAAAGAG TCGAAATCAG     840

CTAATGAAAT TTCACCTGAG CAAATTAACC AATGGATTAA AGAACACCAA GAAAATAAGA     900

ATACAGATGC ACAGGATAAG TTAGTTAAAC ATTACCAAAA ACTAATTGAG TCATTGGCAT     960

ATAAATATTC TAAAGGACAA TCACATCACG AAGATTTAGT TCAAGTTGGT ATGGTTGGTT    1020

TAATAGGTGC CATAAATAGA TTCGATATGT CCTTTGAACG GAAGTTTGAA GCCTTTTTAG    1080

TACCTACTGT AATCGGTGAA ATCAAAAGAT ATCTACGAGA TAAAACTTGG AGTGTACATG    1140

TTCCGAGACG TATTAAAGAA ATTGGGCCAA GAATCAAAAA AGTGAGCGAT GAACTAACCG    1200

CTGAATTAGA GCGTTCACCT TCTATCAGTG AAATAGCTGA TCGATTAGAA GTCTCAGAAG    1260
```

-continued

```
AAGAAGTGTT AGAAGCAATG GAAATGGGAC AAAGTTATAA TGCGTTAAGT GTTGATCATT    1320

CCATTGAAGC TGATAAAGAT GGTTCAACTG TTACGCTATT AGATATTATG GGGCAACAAG    1380

ATGACCATTA TGACTTAACT GAAAAACGTA TGATTTTAGA AAAAATATTA CCTATATTAT    1440

CTGATCGCGA ACGAGAAATC ATACAATGTA CGTTTATTGA AGGATTGAGT CAAAAAGAGA    1500

CAGGTGAGCG TATCGGTTTA AGTCAAATGC ATGTATCACG ACTTCAGAGA ACGGCAATTA    1560

AGAAATTACA AGAAGCAGCA CATCAATAGA ATTTGTTTAT TAATGATACG TTTTATAATG    1620

AAAAATCCAT ATAATTATCC CTTGATTATT AAATTGAAAT CGAGGGGTAT TTTTAATTTA    1680

ATTAAGATTT TCGAATTAAT ACATTATTAG TGTAGTTTAA TGTGTATCCA CATAAATGTC    1740

GCGATATAGT ATTAATAATT TAAGTGAAGA AGATATCTAA TTGTCGTTTT AAATAGGTGG    1800

GTTGCTATTA GAATAAAAAA AGTAGTCTTA GATTATGAAA TTTAGAAATG ATGGTGTGTC    1860

ATTTTCAATA ATCTTAGTGC GTTTTAAAAT ATAGTATGAC CTAATCATTC GTTTTAAATG    1920

TTTTGGAAGT GAAAATTACA TTAAGTATCA TACCTTAATA GAAGTATTTT AGAATATGTT    1980

AAAATAAATG AGTAAATTTA AGAAAAAGTG TGGGTTAAGT AAATGGACAA TCAATTGATT    2040

AATTCAATCA TAGAGAAATA TCAATTTAGT AAAAAACAAA TTGAAGCAGT ATTAACACTG    2100

CTAGAAGAAA AAAATACAGT ACCATTTATT GCGAGGTATC GAAAAGAGCA AACTGGTGGA    2160

CTAGATGAAG TTCAAATAAA GCAAATTGAT GACGAATACC AATATATGGT CAATTTACAA    2220

AAACGTAAAG AAGAAGTTAT CAAAAATATA GAACAGCAAG GATTACTTAC TGAGGAATTA    2280

AAGAAGGATA TTTTAAAACA GAACAAATTA CAACGTGTTG AAGACCTATA TAGGCCTTTT    2340

AAACAAAAGA AAAAGACAAG GGCAACTGAG GCGAAACGTA AAGGGTTAGA GCCATTAGCG    2400

ATATGGATGA AGGCACGTAA ACATGAAGTC TCAATTGAAG AAAAAGCACA ACAATTTATA    2460

AATGAAGAAG TGCAATCGGT TGAAGATGCT ATCAAAGGTG CACAAGATAT TATTGCGGAA    2520

CAAATTTCAG ATAATCCTAA ATATAGAACA AAAATTTTAA AAGATATGTA TCATCAAGGT    2580

GTGTTAACTA CATCTAAAAA GAAAAATGCT GAAGATGAAA AAGGTATTTT TGAAATGTAC    2640

TATGCATATA GTGAGCCAAT TAAACGCATT GCTAATCATA GAGTTTTAGC TGTTAATCGT    2700

GGTGAAAAAG AGAAAGTATT ATCTGCAAAG TTTGAATTC                          2739
```